United States Patent
Hauswirth et al.

(10) Patent No.: US 10,648,000 B2
(45) Date of Patent: May 12, 2020

(54) RAAV VECTOR COMPOSITIONS, METHODS FOR TARGETING VASCULAR ENDOTHELIAL CELLS AND USE IN TREATMENT OF TYPE I DIABETES

(71) Applicant: University of Florida Research Foundation, Incorporated, Gainesville, FL (US)

(72) Inventors: William W. Hauswirth, Gainesville, FL (US); Sanford L. Boye, Gainesville, FL (US); Daniel M. Lipinski, Milwaukee, WI (US); Michael E. Boulton, Chelsea, AL (US); Shannon E. Boye, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 107 days.

(21) Appl. No.: 15/550,864

(22) PCT Filed: Feb. 16, 2016

(86) PCT No.: PCT/US2016/018098
§ 371 (c)(1),
(2) Date: Aug. 14, 2017

(87) PCT Pub. No.: WO2016/133917
PCT Pub. Date: Aug. 25, 2016

(65) Prior Publication Data
US 2018/0057840 A1    Mar. 1, 2018

Related U.S. Application Data

(60) Provisional application No. 62/116,863, filed on Feb. 16, 2015.

(51) Int. Cl.
| | |
|---|---|
| *C12N 15/86* | (2006.01) |
| *C12N 9/78* | (2006.01) |
| *A61K 38/50* | (2006.01) |
| *A61K 48/00* | (2006.01) |
| *C07K 14/005* | (2006.01) |
| *C07K 14/705* | (2006.01) |
| *C12N 7/00* | (2006.01) |
| *A61K 38/00* | (2006.01) |

(52) U.S. Cl.
CPC .............. *C12N 15/86* (2013.01); *A61K 38/50* (2013.01); *A61K 48/0058* (2013.01); *C07K 14/005* (2013.01); *C07K 14/705* (2013.01); *C12N 7/00* (2013.01); *C12N 9/78* (2013.01); *C12Y 305/04016* (2013.01); *A61K 38/00* (2013.01); *C12N 2750/14121* (2013.01); *C12N 2750/14122* (2013.01); *C12N 2750/14143* (2013.01); *C12N 2830/008* (2013.01); *C12N 2830/15* (2013.01); *C12N 2830/85* (2013.01)

(58) Field of Classification Search
CPC . C12N 15/86; C12N 7/00; C12N 9/78; C12N 2750/14121; C12N 2750/14122; C12N 2750/14143; C12N 2830/008; C12N 2830/15; C12N 2830/85; A61K 38/50; A61K 48/0058; A61K 38/00; C07K 14/005; C12Y 305/04016
See application file for complete search history.

(56) References Cited

U.S. PATENT DOCUMENTS

| | | |
|---|---|---|
| 6,162,796 A | 12/2000 | Kaplitt et al. |
| 6,479,654 B1 | 11/2002 | Baird et al. |
| 8,445,267 B2 | 5/2013 | Zhong et al. |
| 8,802,080 B2 | 8/2014 | Warrington et al. |
| 8,802,440 B2 | 8/2014 | Zhong et al. |
| 9,157,098 B2 | 10/2015 | Zhong et al. |
| 9,611,302 B2 | 4/2017 | Srivastava et al. |
| 9,725,485 B2 | 8/2017 | Srivastava et al. |

(Continued)

FOREIGN PATENT DOCUMENTS

| | | |
|---|---|---|
| EP | 1 486 567 A1 | 12/2004 |
| WO | WO 2007/089632 A2 | 8/2007 |

(Continued)

OTHER PUBLICATIONS

Dong et al., Adv Drug Deliv Rev. Jul. 2, 2009; 61(7-8): 542-553.*
International Search Report and Written Opinion for Application No. PCT/US2016/018098 dated May 23, 2015.
International Preliminary Report on Patentability for Application No. PCT/US2016/018098 dated Aug. 31, 2017.
Drouin et al., Adeno-associated virus structural biology as a tool in vector development. Future Virology. Dec. 2013;8(12):1183-1199. Author manuscript.

(Continued)

*Primary Examiner* — Thaian N. Ton
(74) *Attorney, Agent, or Firm* — Wolf, Greenfield & Sacks, P.C.

(57) ABSTRACT

Disclosed are capsid-modified rAAV expression vectors, as well as infectious virions, compositions, and pharmaceutical formulations that include them. Also disclosed are methods of preparing and using novel capsid-protein-mutated rAAV vector constructs in a variety of diagnostic and therapeutic applications including, inter alia, as delivery agents for diagnosis, treatment, or amelioration of one or more diseases, disorders, or dysfunctions of the mammalian vascular system, and complications from Type I diabetes. Also disclosed are methods for systemic and tissue-localized delivery of therapeutic rAAV-based gene expression cassettes to vascular endothelial cells, tissues, and organs, as well as use of the disclosed compositions in the manufacture of medicaments for a variety of in vitro and/or in vivo applications including the treatment of vasculitis, and complications arising from Type I diabetes, such as macular edema, nephropathy, diabetic retinopathy, and the like.

13 Claims, 9 Drawing Sheets
Specification includes a Sequence Listing.

(56) References Cited

U.S. PATENT DOCUMENTS

| | | | |
|---|---|---|---|
| 9,775,918 | B2 | 10/2017 | Zhong et al. |
| 9,920,097 | B2 | 3/2018 | Zhong et al. |
| 10,011,640 | B2 | 7/2018 | Srivastava et al. |
| 10,294,281 | B2 | 5/2019 | Srivastava et al. |
| 10,308,957 | B2 * | 6/2019 | Boye .................. A61K 9/0048 |
| 2005/0053590 | A1 | 3/2005 | Meininger |
| 2006/0088936 | A1 | 4/2006 | Warrington et al. |
| 2010/0069467 | A1 | 3/2010 | Boye et al. |
| 2010/0203083 | A1 | 8/2010 | Lux et al. |
| 2010/0260800 | A1 | 10/2010 | Bartlett et al. |
| 2013/0310443 | A1 | 11/2013 | Srivastava et al. |
| 2014/0050701 | A1 | 2/2014 | Zhong et al. |
| 2014/0341852 | A1 | 11/2014 | Srivastava et al. |
| 2015/0005369 | A1 | 1/2015 | Muzyczka et al. |
| 2016/0333372 | A1 | 11/2016 | Srivastava et al. |
| 2017/0275337 | A1 | 9/2017 | Srivastava et al. |
| 2018/0030096 | A1 | 2/2018 | Aslanidi et al. |
| 2018/0036428 | A1 | 2/2018 | Zhong et al. |
| 2018/0105559 | A1 | 4/2018 | Zhong et al. |
| 2018/0223312 | A1 | 8/2018 | Srivastava et al. |
| 2018/0244727 | A1 | 8/2018 | Zhong et al. |
| 2019/0016759 | A1 | 1/2019 | Srivastava et al. |
| 2019/0127424 | A1 | 5/2019 | Srivastava et al. |
| 2019/0284244 | A1 | 9/2019 | Srivastava et al. |

FOREIGN PATENT DOCUMENTS

| | | | |
|---|---|---|---|
| WO | WO 2010/011404 A2 | 1/2010 | |
| WO | WO 2010/093784 A2 | 8/2010 | |
| WO | WO 2012/145601 A2 | 10/2012 | |
| WO | WO 2013/158879 A1 | 10/2013 | |
| WO | WO 2013/173512 A2 | 11/2013 | |
| WO | WO 2015/126972 A1 | 8/2015 | |

OTHER PUBLICATIONS

Galeano et al., Adeno-associated viral vector-mediated human vascular endothelial growth factor gene transfer stimulates angiogenesis and wound healing in the genetically diabetic mouse. Diabetologia. Apr. 2003;46:546-555.
Heitzer et al., Tetrahydrobiopterin improves endothelium-dependent vasodilation by increasing nitric oxide activity in patients with Type II diabetes mellitus. Diabetologia. 2002;43:1435-1438.
Higashi et al., Tetrahydrobiopterin enhances forearm vascular response to acetylcholine in both normotensive and hypertensive individuals. Am. J. Hypertens. 2002;15:326-332.
Lipinski et al., Systematic Vascular Transduction by Capsid Mutant Adeno-Associated Virus After Intravenous Injection. Human Gene Therapy. Nov. 2015.; 26(11): 767-776.
Meininger et al., GTP cyclohydrolase I gene transfer reverses tetrahydrobiopterin deficiency and increases nitric oxide synthesis in endothelial cells and isolated vessels from diabetic rats. FASEB J. 2004;18(15):1900-1902.
Melo et al., Endothelium-Targeted Gene and Cell-Based Therapies for Cardiovascular Disease. Arteriosclerosis, Thrombosis, and Vascular Biology. 2004;24:1761-1774.
Nicklin et al., Efficient and selective AAV2-mediated gene transfer directed to human vascular endothelial cells. Molecular Therapy. 2001;4(3):174-181.
Pieper, Acute amelioration of diabetic endothelial dysfunction with a derivative of the nitric oxide synthase cofactor, tetrahydrobiopterin. J. Cardiovasc. Pharmacol. 1997;29:8-15.
Powell et al., Viral expression cassette elements to enhance transgene target specificity and expression in gene therapy. Discovery Medicine. Jan. 2015;19(102):49-57. Author manuscript.
Qi et al., γ-Secretase Inhibition of Murine Choroidal Neovascularization Is Associated with Reduction of Superoxide and Proinflammatory Cytokines. Investigative Ophthalmology & Visual Science. Feb. 2012;53(2):574-575.
Ruan et al., Development of an anti-angiogenic therapeutic model combining scAAV2-delivered siRNAs and noninvasive photoacoustic imaging of tumor vasculature development. Cancer Letters. Nov. 2012;332(1):120-129.
Stroes et al., Tetrahydrobiopterin restores endothelial function in hypercholesterolemia. J. Clin. Invest. 1997;99:41-46.
White et al., Targeted Gene Delivery to Vascular Tissue in Vivo by Tropism-Modified Adeno-Associated Virus Vectors. Circulation. 2004;109L513-519.
Xu et al., Molecular Insights and Therapeutic Targets for Diabetic Endothelial Dysfunction. Circulation. Sep. 2009; 120(13):1266-1286.
International Preliminary Report on Patentability dated Sep. 15, 2016 for Application No. PCT/US2015/018791.
International Search Report and Written Opinion dated Aug. 12, 2015 for Application No. PCT/US2015/018791.
Extended European Search Report dated Nov. 3, 2017 for Application No. EP 15758026.7.
Aslanidi et al, High-Efficiency Transduction of Human Monocyte-Derived Dendritic Cells by Capsid-Modified Recombinant AAV2 Vectors. Vaccine. Jun. 6, 2012; 30(26):3908-17. Author manuscript.
Aslanidi et al, Optimization of the Capsid of Recombinant Adeno-Associated Virus 2 (AAV2) Vectors: The Final Threshold?. PLoS One. 2013;8(3):e59142. doi: 10.1371/journal.pone.0059142. Epub Mar. 19, 2013 (12 pages).
Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. May 2013; 21(S1):S129.
Aslanidi et al., Abstract 334: Optimization of the capsid of recombinant adeno-associated virus 2 (AAV2) vectors: the final threshold? Molecular Therapy. May 2013; 21(S1):S129.
Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 10, 2011(11): Abstract C240. 3 Pages.
Boye et al., Impact of Heparan Sulfate Binding on Transduction of Retina by Recombinant Adeno-Associated Virus Vectors. J Virol. Mar. 28, 2016; 90(8):4215-4231. doi: 10.1128/JVI.00200-16. Print Apr. 2016.
Cheng et al, Development of Optimized AAV3 Serotype Vectors: Mechanism of High-Efficiency Transduction of Human Liver Cancer Cells. Gene Ther. Apr. 2012; 19(4):375-84.
Doroudchi et al., Virally Delivered Channeirhodopsin-2 Safely and Effectively Restores Visual Function in Multiple Mouse Models of Blindness. Mol Ther. Jul. 2011; 19(7):1220-9.
Gabriel et al., Targeted Mutagenesis of Ubiquitin-Binding Lysine Residues on the Adeno-Associated Virus (AAV)2 Capsid Improves Its Transduction Efficiency. Mol Ther. 2012; 20(Supp 1):S146.
Jayandharan et al., Activation of the NF-κB Pathway by Adeno-Associated Virus (AAV) Vectors and its Implications in Immune Response and Gene Therapy. Proc Natl Acad Sci U S A. Mar. 1, 2011; 108(9):3743-8. Retraction in: PNAS Jan. 9, 2018. 115 (2) E343; published ahead of print Dec. 26, 2017.
Kauss et al., Enhanced Long-Term Transduction and Multilineage Engraftment of Human Hematopoietic Stem Cells Transduced With Tyrosine-Modified Recombinant Adeno-Associated Virus Serotype 2. Hum Gene Ther. Sep. 2010; 21(9):1129-36.
Kay et al., Targeting photoreceptors via intravitreal delivery using novel, capsid-mutated AAV vectors. PLoS One. Apr. 26, 2013; 8(4):e62097. doi: 10.1371/journal.pone.0062097. Print 2013.
Ku et al., Gene Therapy Using Self-Complementary T733F Capsid Mutant AAV2/8 Restores Vision in a Model of Early Onset Leber Congenital Amaurosis. Hum Mol Genet. Dec. 1, 2011; 20(23):4569-81.
Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013; 21(Supp 1):S208-9.
Ling et al, Selective in vivo targeting of human liver tumors by optimized AAV3 vectors in a murine xenograft model. Hum Gene Ther. Dec. 2014; 25(12):1023-34. doi: 10.1089/hum.2014.099.
Lochrie et al., Mutations on the external surfaces of adeno-associated virus type 2 capsids that affect transduction and neutralization. J Virol. Jan. 2006; 80(2):821-34.

(56) References Cited

OTHER PUBLICATIONS

Markusic et al., High-Efficiency Transduction and Correction of Murine Hemophelia B Using AAV2 Vectors Devoid of Multiple Surface-Exposed Tyrosines. Mol Ther. Dec. 2010; 18(12):2048-56.
Nonnenmacher et al., Intracellular Transport of Recombinant Adeno-Associated Virus Vectors. Gene Therapy. Jun. 2012; 19(6):649-658.
O'Donnell et al., Adeno-associated virus-2 and its primary cellular receptor—Cryo-EM structure of a heparin complex. Virology. Mar. 15, 2009; 385(2):434-43. doi: 10.1016/j.virol.2008.11.037. Epub Jan. 13, 2009.
Opie et al., Identification of amino acid residues in the capsid proteins of adeno-associated virus type 2 that contribute to heparan sulfate proteoglycan binding J Virol. Jun. 2003; 77(12):6995-7006.
Pang et al., Long-Term Retinal Function and Structure Rescue Using Capsid Mutant AAV8 Vector in the rd10 Mouse, a Model or Recessive Retinitis Pigmentosa. Mol Ther. Feb. 2011; 19(2):234-42. doi: 10.1038/mt.2010.273. Epub Dec. 7, 2010.
Petrs-Silva et al., High-Efficiency Transduction of the Mouse Retina by Tyrosine-Mutant AAV Serotype Vectors. Mol Ther. Mar. 2009; 17(3):463-71.
Petrs-Silva et al., Novel Properties of Tyrosine-Mutant AAV2 Vectors in the Mouse Retina. Mol Ther. Feb. 2011; 19(2):293-301.
Qiao et al., Adeno-Associated Virus Serotype 6 Capsid Tyrosine-to-Phenylalanine Mutations Improve Gene Transfer to Skeletal Muscle. Hum Gene Ther. Oct. 2010; 21(10):1343-8.
Ruan et al., Development of an Anti-Angiogenic Therapeutic Model Combining scAAV2-delivered siRNAs and Noninvasive Photoacoustic Imaging of Tumor Vasculature Development. Cancer Lett. May 10, 2013; 332(1):120-9. doi: 10.1016/j.canlet.2012.11.016. Epub Nov. 27, 2012.
Ryals et al., Quantifying Transduction Efficiencies of Unmodified and Tyrosine Capsid Mutant AAV Vectors in Vitro Using Two Ocular Cell Lines. Mol Vis. Apr. 29, 2011; 17:1090-102.
Shin et al., A Simplified Immune Suppression Scheme Leads to Persistent Micro-Dystrophin Expression in Duchenne Muscular Dystrophy Dogs. Hum Gene Ther. Feb. 2012; 23(2):202-9. doi: 10.1089/hum.2011.147. Epub Dec. 14, 2011.
Song et al., High-efficiency transduction of primary human hematopoietic stem cells and erythroid lineage-restricted expression by optimized AAV6 serotype vectors in vitro and in a murine xenograft model in vivo. PLoS One. 2013; 8(3):e58757. doi: 10.1371/journal.pone.0058757. Epub Mar. 14, 2013.
Vandenberghe et al., Naturally occurring singleton residues in AAV capsid impact performance and illustrate structural constraints. Gene Ther. Dec. 2009; 16(12):1416-28. doi: 10.1038/gt.2009.101.
Wang et al., Limitations of encapsidation of recombinant self-complementary adeno-associated viral genomes in different serotype capsids and their quantitation. Hum Gene Ther Methods. Aug. 2012; 23(4):225-33. doi: 10.1089/hgtb.2012.090.
Warrington et al., Adeno-associated virus type 2 VP2 capsid protein is nonessential and can tolerate large peptide insertions at its N terminus. Journal of Virology. Jun. 2004; 78(12);6595-6609.
Zhong et al., A Dual Role of EGFR Protein Tyrosine Kinase Signaling in Ubiquitination of AAV2 Capsids and Viral Second-strand DNA Synthesis. Mol Ther. Jul. 2007; 15(7):1323-30. Epub Apr. 17, 2007.
Zhong et al., Evaluation of Primitive Murine Hematopoietic Stem and Progenitor Cell Transduction In Vitro and In Vivo by Recombinant Adeno-Associated Virus Vector Serotypes 1 Through 5. Hum Gene Ther. Mar. 2006; 17(3):321-33.
Zhong et al., Next generation of adeno-associated virus 2 vectors: Point mutations in tyrosines lead to high-efficiency transduction at lower doses. Proc Natl Acad Sci U S A. Jun. 3, 2008; 105(22):7827-32. doi: 10.1073/pnas.0802866105. Epub May 29, 2008.

* cited by examiner

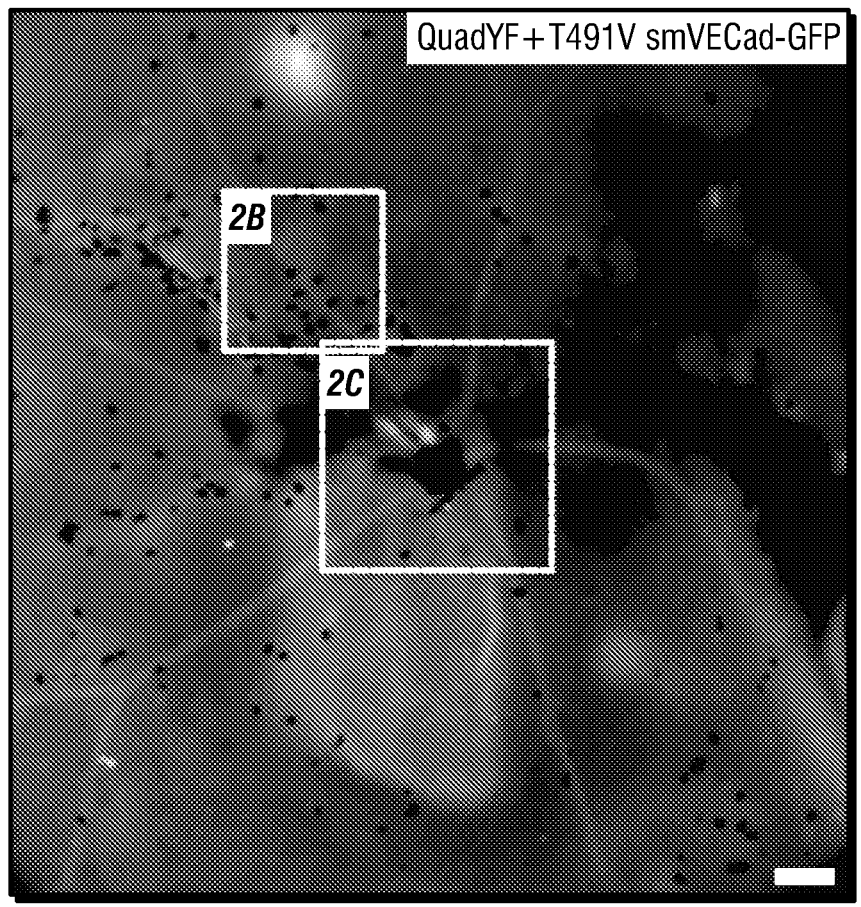
FIG. 2A
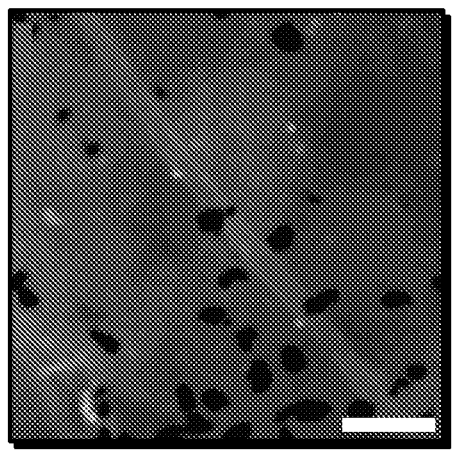 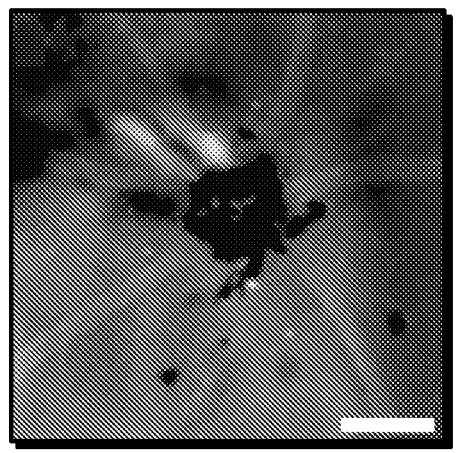
FIG. 2B  FIG. 2C

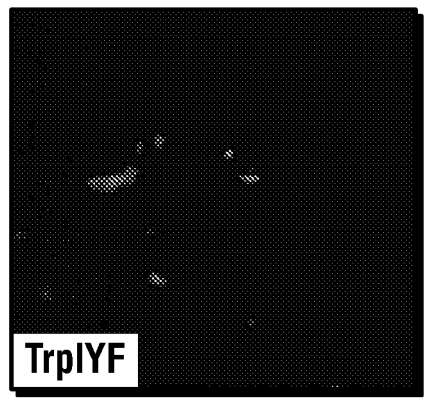
FIG. 3A  FIG. 3B
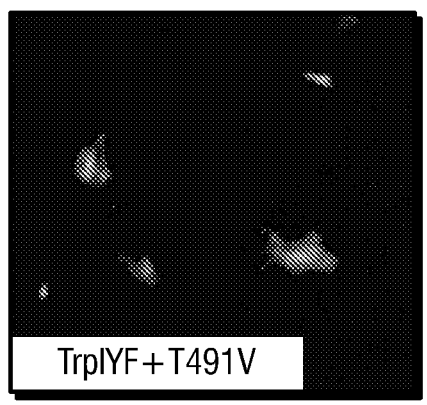
FIG. 3C
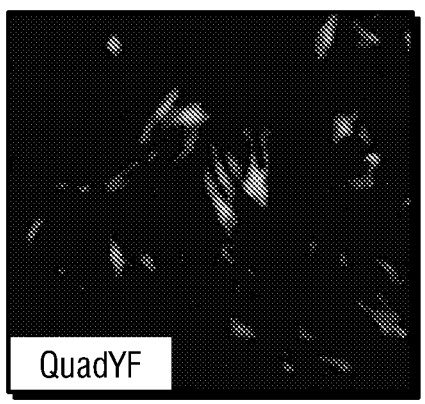
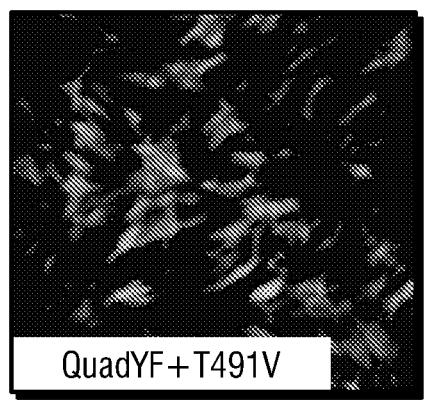
FIG. 3D  FIG. 3E

SEQUENCE LISTING

```
<160> NUMBER OF SEQ ID NOS: 10

<210> SEQ ID NO 1
<211> LENGTH: 728
<212> TYPE: PRT
<213> ORGANISM: adeno-associated virus 1

<400> SEQUENCE: 1

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Gly Lys Lys Arg Pro Val
    130                 135                 140

Glu Gln Ser Pro Gln Glu Pro Asp Ser Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Leu Ile Asn Asn Asn Trp Gly Phe Arg
    290                 295                 300

Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
```

```
            340                 345                 350
Ser Ala His Gln Gly Cys Leu Pro Pro Phe Pro Ala Asp Val Phe Met
            355                 360                 365
Ile Pro Gln Tyr Gly Tyr Leu Thr Leu Asn Asn Gly Ser Gln Ala Val
            370                 375                 380
Gly Arg Ser Ser Phe Tyr Cys Glu Tyr Phe Pro Ser Gln Met Leu Arg
385                 390                 395                 400
Thr Gly Asn Asn Phe Thr Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Asn Arg Thr Gln Asn Gln Ser
            435                 440                 445
Gly Ser Ala Gln Asn Lys Asp Leu Leu Phe Ser Arg Gly Ser Pro Ala
            450                 455                 460
Gly Met Ser Val Gln Pro Lys Asn Trp Leu Pro Gly Pro Cys Tyr Arg
465                 470                 475                 480
Gln Gln Arg Val Ser Lys Thr Lys Thr Asn Asn Asn Ser Asn Phe Thr
                485                 490                 495
Trp Thr Gly Ala Ser Lys Tyr Asn Leu Asn Gly Arg Glu Ser Ile Ile
            500                 505                 510
Asn Pro Gly Thr Ala Met Ala Ser His Lys Asp Asp Glu Asp Lys Phe
            515                 520                 525
Phe Pro Met Ser Gly Val Met Ile Phe Gly Lys Glu Ser Ala Gly Ala
            530                 535                 540
Ser Asn Thr Ala Leu Asp Asn Val Met Ile Thr Asp Glu Glu Glu Ile
545                 550                 555                 560
Lys Ala Thr Asn Pro Val Ala Thr Glu Arg Phe Gly Thr Val Ala Val
                565                 570                 575
Asn Phe Gln Ser Ser Thr Asp Pro Ala Thr Gly Asp Val His Ala Met
            580                 585                 590
Gly Ala Leu Pro Gly Met Val Trp Gln Asp Arg Asp Val Tyr Leu Gln
            595                 600                 605
Gly Pro Ile Trp Ala Lys Ile Pro His Thr Asp Gly His Phe His Pro
            610                 615                 620
Ser Pro Leu Met Gly Gly Phe Gly Leu Lys Asn Pro Pro Pro Gln Ile
625                 630                 635                 640
Leu Ile Lys Asn Thr Pro Val Pro Ala Asn Pro Ala Glu Phe Ser
                645                 650                 655
Ala Thr Lys Phe Ala Ser Phe Ile Thr Gln Tyr Ser Thr Gly Gln Val
            660                 665                 670
Ser Val Glu Ile Glu Trp Glu Gln Lys Glu Asn Ser Lys Arg Trp Asn
            675                 680                 685
Pro Glu Val Gln Tyr Thr Ser Asn Tyr Ala Lys Ser Ala Asn Val Asp
            690                 695                 700
Phe Thr Val Asp Asn Asn Gly Leu Tyr Thr Glu Pro Arg Pro Ile Gly
705                 710                 715                 720
Thr Arg Tyr Leu Thr Arg Pro Leu
                725

<210> SEQ ID NO 2
<211> LENGTH: 727
<212> TYPE: PRT
<213> ORGANISM: adeno-associated virus 2
```

```
<400> SEQUENCE: 2

Ala Ala Asp Gly Tyr Leu Pro Asp Trp Leu Glu Asp Thr Leu Ser Glu
1               5                   10                  15

Gly Ile Arg Gln Trp Trp Lys Leu Lys Pro Gly Pro Pro Pro Pro Lys
            20                  25                  30

Pro Ala Glu Arg His Lys Asp Asp Ser Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Glu Ala Asp Ala Ala Leu Glu His Asp Lys Ala Tyr Asp Arg
65                  70                  75                  80

Gln Leu Asp Ser Gly Asp Asn Pro Tyr Leu Lys Tyr Asn His Ala Asp
                85                  90                  95

Ala Glu Phe Glu Arg Leu Lys Glu Asp Thr Ser Phe Gly Gly Asn Leu
            100                 105                 110

Gly Arg Ala Val Phe Gln Ala Lys Lys Arg Val Leu Glu Pro Leu Gly
            115                 120                 125

Leu Val Glu Glu Pro Val Lys Thr Ala Pro Gly Lys Lys Arg Pro Val
130                 135                 140

Glu His Ser Pro Val Glu Pro Asp Ser Ser Ser Gly Thr Gly Lys Ala
145                 150                 155                 160

Gly Gln Gln Pro Ala Arg Lys Arg Leu Asn Phe Gly Gln Thr Gly Asp
                165                 170                 175

Ala Asp Ser Val Pro Asp Pro Gln Pro Leu Gly Gln Pro Pro Ala Ala
            180                 185                 190

Pro Ser Gly Leu Gly Asn Thr Met Ala Thr Gly Ser Gly Ala Pro Met
            195                 200                 205

Ala Asp Asn Asn Glu Gly Ala Asp Gly Val Gly Asn Ser Ser Gly Asn
210                 215                 220

Trp His Cys Asp Ser Thr Trp Met Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Gln Ser Gly Ala Ser Asn Asp Asn His Tyr Phe Gly Tyr
            260                 265                 270

Ser Thr Pro Trp Gly Tyr Phe Asp Phe Asn Arg Phe His Cys His Phe
            275                 280                 285

Ser Pro Arg Asp Trp Gln Leu Ile Asn Asn Asn Trp Gly Phe Arg Pro
        290                 295                 300

Lys Arg Leu Asn Phe Lys Leu Phe Asn Ile Gln Val Lys Glu Val Thr
305                 310                 315                 320

Gln Asn Asp Gly Thr Thr Thr Ile Ala Asn Asn Leu Thr Ser Thr Val
                325                 330                 335

Gln Val Phe Thr Asp Ser Glu Tyr Gln Leu Pro Tyr Val Leu Gly Ser
            340                 345                 350

Ala His Gln Gly Cys Leu Pro Pro Phe Pro Ala Asp Val Phe Met Val
            355                 360                 365

Pro Gln Tyr Gly Tyr Leu Thr Leu Asn Asn Gly Ser Gln Ala Val Gly
            370                 375                 380

Arg Ser Ser Phe Tyr Cys Glu Tyr Phe Pro Ser Gln Met Leu Arg Thr
385                 390                 395                 400

Gly Asn Asn Phe Thr Phe Ser Tyr Thr Phe Glu Asp Val Pro Phe His
```

```
            405                 410                 415
Ser Ser Tyr Ala His Ser Gln Ser Leu Asp Arg Leu Met Asn Pro Leu
                420                 425                 430

Ile Asp Gln Tyr Leu Tyr Tyr Leu Ser Arg Thr Asn Thr Pro Ser Gly
            435                 440                 445

Thr Thr Thr Gln Ser Arg Leu Gln Phe Ser Gln Ala Gly Ala Ser Asp
        450                 455                 460

Ile Arg Asp Gln Ser Arg Asn Trp Leu Pro Gly Pro Cys Tyr Arg Gln
465                 470                 475                 480

Gln Arg Val Ser Lys Thr Ser Ala Asn Asn Asn Ser Glu Tyr Ser Trp
                485                 490                 495

Thr Gly Ala Thr Lys Tyr His Leu Asn Gly Arg Asp Ser Leu Val Asn
            500                 505                 510

Pro Gly Pro Ala Met Ala Ser His Lys Asp Asp Glu Glu Lys Phe Phe
        515                 520                 525

Pro Gln Ser Gly Val Leu Ile Phe Gly Lys Gln Gly Ser Glu Lys Thr
    530                 535                 540

Asn Val Asp Ile Glu Lys Val Met Ile Thr Asp Glu Glu Ile Arg
545                 550                 555                 560

Thr Thr Asn Pro Val Ala Thr Glu Gln Tyr Gly Ser Val Ser Thr Asn
                565                 570                 575

Leu Gln Arg Asn Arg Gln Ala Ala Thr Ala Asp Val Asn Thr Gln Gly
            580                 585                 590

Val Leu Pro Gly Met Val Trp Gln Asp Arg Asp Val Tyr Leu Gln Gly
        595                 600                 605

Pro Ile Trp Ala Lys Ile Pro His Thr Asp Gly His Phe His Pro Ser
610                 615                 620

Pro Leu Met Gly Gly Phe Gly Leu Lys His Pro Pro Pro Gln Ile Leu
625                 630                 635                 640

Ile Lys Asn Thr Pro Val Pro Ala Asn Pro Ser Thr Thr Phe Ser Ala
                645                 650                 655

Ala Lys Phe Ala Ser Phe Ile Thr Gln Tyr Ser Thr Gly Gln Val Ser
            660                 665                 670

Val Glu Ile Glu Trp Glu Gln Lys Glu Asn Ser Lys Arg Trp Asn Pro
        675                 680                 685

Glu Ile Gln Tyr Thr Ser Asn Tyr Asn Lys Ser Val Asn Val Asp Phe
    690                 695                 700

Thr Val Asp Thr Asn Gly Val Tyr Ser Glu Pro Arg Pro Ile Gly Thr
705                 710                 715                 720

Arg Tyr Leu Thr Arg Asn Leu
                725

<210> SEQ ID NO 3
<211> LENGTH: 728
<212> TYPE: PRT
<213> ORGANISM: adeno-associated virus 3

<400> SEQUENCE: 3

Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Val Pro Gln Pro Lys
            20                  25                  30

Ala Asn Gln Gln His Gln Asp Asn Arg Arg Gly Leu Val Leu Pro Gly
        35                  40                  45
```

-continued

Tyr Lys Tyr Leu Gly Pro Gly Asn Gly Leu Asp Lys Gly Glu Pro Val
 50                  55                  60

Asn Glu Ala Asp Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Glu Arg Leu Gln Glu Asp Thr Ser Phe Gly Gly Asn Leu
             100                 105                 110

Gly Arg Ala Val Phe Gln Ala Lys Lys Arg Ile Leu Glu Pro Leu Gly
         115                 120                 125

Leu Val Glu Ala Ala Lys Thr Ala Pro Gly Lys Lys Gly Ala Val
130                 135                 140

Asp Gln Ser Pro Gln Glu Pro Asp Ser Ser Ser Gly Val Gly Lys Ser
145                 150                 155                 160

Gly Lys Gln Pro Ala Arg Lys Arg Leu Asn Phe Gly Gln Thr Gly Asp
                 165                 170                 175

Ser Glu Ser Val Pro Asp Pro Gln Pro Leu Gly Glu Pro Ala Ala
             180                 185                 190

Pro Thr Ser Leu Gly Asn Thr Met Ala Ser Gly Gly Ala Pro Met
         195                 200                 205

Ala Asp Asn Asn Glu Gly Ala Asp Gly Val Gly Asn Ser Ser Gly Asn
210                 215                 220

Trp His Cys Asp Ser Gln Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                 245                 250                 255

Ile Ser Ser Gln Ser Gly Ala Ser Asn Asp Asn His Tyr Phe Gly Tyr
             260                 265                 270

Ser Thr Pro Trp Gly Tyr Phe Asp Phe Asn Arg Phe His Cys His Phe
         275                 280                 285

Ser Pro Arg Asp Trp Gln Leu Ile Asn Asn Asn Trp Gly Phe Arg Pro
290                 295                 300

Lys Lys Leu Ser Phe Lys Leu Phe Asn Ile Gln Val Arg Gly Val Thr
305                 310                 315                 320

Gln Asn Asp Gly Thr Thr Thr Ile Ala Asn Asn Leu Thr Ser Thr Val
                 325                 330                 335

Gln Val Phe Thr Asp Ser Glu Tyr Gln Leu Pro Tyr Val Leu Gly Ser
             340                 345                 350

Ala His Gln Gly Cys Leu Pro Pro Phe Pro Ala Asp Val Phe Met Val
         355                 360                 365

Pro Gln Tyr Gly Tyr Leu Thr Leu Asn Asn Gly Ser Gln Ala Val Gly
370                 375                 380

Arg Ser Ser Phe Tyr Cys Glu Tyr Phe Pro Ser Gln Met Leu Arg Thr
385                 390                 395                 400

Gly Asn Asn Phe Gln Phe Ser Tyr Thr Phe Glu Asp Val Pro Phe His
                 405                 410                 415

Ser Ser Tyr Ala His Ser Gln Ser Leu Asp Arg Leu Met Asn Pro Leu
             420                 425                 430

Ile Asp Gln Tyr Leu Tyr Leu Asn Arg Thr Gln Gly Thr Thr Ser
         435                 440                 445

Gly Thr Thr Asn Gln Ser Arg Leu Leu Phe Ser Gln Ala Gly Pro Gln
450                 455                 460

Ser Met Ser Leu Gln Ala Arg Asn Trp Leu Pro Gly Pro Cys Tyr Arg

```
                465                 470                 475                 480
Gln Gln Arg Leu Ser Lys Thr Ala Asn Asn Asn Ser Asn Phe Pro
                485                 490                 495

Trp Thr Ala Ala Ser Lys Tyr His Leu Asn Gly Arg Asp Ser Leu Val
                500                 505                 510

Asn Pro Gly Pro Ala Met Ala Ser His Lys Asp Asp Glu Glu Lys Phe
                515                 520                 525

Phe Pro Met His Gly Asn Leu Ile Phe Gly Lys Glu Gly Thr Thr Ala
                530                 535                 540

Ser Asn Ala Glu Leu Asp Asn Val Met Ile Thr Asp Glu Glu Glu Ile
545                 550                 555                 560

Arg Thr Thr Asn Pro Val Ala Thr Glu Gln Tyr Gly Thr Val Ala Asn
                565                 570                 575

Asn Leu Gln Ser Asn Thr Ala Pro Thr Thr Gly Thr Val Asn His Gln
                580                 585                 590

Gly Ala Leu Pro Gly Met Val Trp Gln Asp Arg Asp Val Tyr Leu Gln
                595                 600                 605

Gly Pro Ile Trp Ala Lys Ile Pro His Thr Asp Gly His Phe His Pro
                610                 615                 620

Ser Pro Leu Met Gly Gly Phe Gly Leu Lys His Pro Pro Gln Ile
625                 630                 635                 640

Met Ile Lys Asn Thr Pro Val Pro Ala Asn Pro Pro Thr Thr Phe Ser
                645                 650                 655

Pro Ala Lys Phe Ala Ser Phe Ile Thr Gln Tyr Ser Thr Gly Gln Val
                660                 665                 670

Ser Val Glu Ile Glu Trp Glu Gln Lys Glu Asn Ser Lys Arg Trp Asn
                675                 680                 685

Pro Glu Ile Gln Tyr Thr Ser Asn Tyr Asn Lys Ser Val Asn Val Asp
                690                 695                 700

Phe Thr Val Asp Thr Asn Gly Val Tyr Ser Glu Pro Arg Pro Ile Gly
705                 710                 715                 720

Thr Arg Tyr Leu Thr Arg Asn Leu
                725

<210> SEQ ID NO 4
<211> LENGTH: 727
<212> TYPE: PRT
<213> ORGANISM: adeno-associated virus 4

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
                35                  40                  45

Tyr Lys Tyr Leu Gly Pro Gly Asn Gly Leu Asp Lys Gly Glu Pro Val
            50                  55                  60

Asn Ala Ala Asp Ala Ala Ala Leu Glu His Asp Lys Ala Tyr Asp Gln
65              70                  75                  80

Gln Leu Lys Ala Gly Asp Asn Pro Tyr Leu Lys Tyr Asn His Ala Asp
                85                  90                  95

Ala Glu Phe Gln Arg Leu Gln Gly Asp Thr Ser Phe Gly Gly Asn Leu
                100                 105                 110
```

```
Gly Arg Ala Val Phe Gln Ala Lys Lys Arg Val Leu Glu Pro Leu Gly
            115                 120                 125
Leu Val Glu Gln Ala Gly Glu Thr Ala Pro Gly Lys Lys Arg Pro Leu
        130                 135                 140
Ile Glu Ser Pro Gln Pro Asp Ser Ser Thr Gly Ile Gly Lys Lys
145                 150                 155                 160
Gly Lys Gln Pro Ala Lys Lys Leu Val Phe Glu Asp Glu Thr Gly
                165                 170                 175
Ala Gly Asp Gly Pro Pro Glu Gly Ser Thr Ser Gly Ala Met Ser Asp
            180                 185                 190
Asp Ser Met Arg Ala Ala Ala Gly Gly Ala Ala Val Glu Gly Gly Gln
        195                 200                 205
Gly Ala Asp Gly Val Gly Asn Ala Ser Gly Asp Trp His Cys Asp Ser
    210                 215                 220
Thr Trp Ser Glu Gly His Val Thr Thr Thr Ser Thr Arg Thr Trp Val
225                 230                 235                 240
Leu Pro Thr Tyr Asn Asn His Leu Tyr Lys Arg Leu Gly Glu Ser Leu
                245                 250                 255
Gln Ser Asn Thr Tyr Asn Gly Phe Ser Thr Pro Trp Gly Tyr Phe Asp
            260                 265                 270
Phe Asn Arg Phe His Cys His Phe Ser Pro Arg Asp Trp Gln Leu Ile
        275                 280                 285
Asn Asn Asn Trp Gly Met Arg Pro Lys Ala Met Arg Val Lys Ile Phe
    290                 295                 300
Asn Ile Gln Val Lys Glu Val Thr Thr Ser Asn Gly Glu Thr Thr Val
305                 310                 315                 320
Ala Asn Asn Leu Thr Ser Thr Val Gln Ile Phe Ala Asp Ser Ser Tyr
                325                 330                 335
Glu Leu Pro Tyr Val Met Asp Ala Gly Gln Glu Gly Ser Leu Pro Pro
            340                 345                 350
Phe Pro Asn Asp Val Phe Met Val Pro Gln Tyr Gly Tyr Cys Gly Leu
        355                 360                 365
Val Thr Gly Asn Thr Ser Gln Gln Gln Thr Asp Arg Asn Ala Phe Tyr
    370                 375                 380
Cys Glu Tyr Phe Pro Ser Gln Met Leu Arg Thr Gly Asn Asn Phe Glu
385                 390                 395                 400
Ile Thr Tyr Ser Phe Glu Lys Val Pro Phe His Ser Met Tyr Ala His
                405                 410                 415
Ser Gln Ser Leu Asp Arg Leu Met Asn Pro Leu Ile Asp Gln Tyr Leu
            420                 425                 430
Trp Gly Leu Gln Ser Thr Thr Thr Gly Thr Thr Leu Asn Ala Gly Thr
        435                 440                 445
Ala Thr Thr Asn Phe Thr Lys Leu Arg Pro Thr Asn Phe Ser Asn Phe
    450                 455                 460
Lys Lys Asn Trp Leu Pro Gly Pro Ser Ile Lys Gln Gln Gly Phe Ser
465                 470                 475                 480
Lys Thr Ala Asn Asn Tyr Lys Ile Pro Ala Thr Gly Ser Asp Ser Leu
                485                 490                 495
Ile Lys Tyr Glu Thr His Ser Thr Leu Asp Gly Arg Trp Ser Ala Leu
            500                 505                 510
Thr Pro Gly Pro Pro Met Ala Thr Ala Gly Pro Ala Asp Ser Lys Phe
        515                 520                 525
Ser Asn Ser Gln Leu Ile Phe Ala Gly Pro Lys Gln Asn Gly Asn Thr
```

-continued

```
                530                 535                 540
Ala Thr Val Pro Gly Thr Leu Ile Phe Thr Ser Glu Glu Leu Ala
545                 550                 555                 560

Ala Thr Asn Ala Thr Asp Thr Asp Met Trp Gly Asn Leu Pro Gly Gly
                565                 570                 575

Asp Gln Ser Ser Asn Leu Pro Thr Val Asp Arg Leu Thr Ala Leu Gly
                580                 585                 590

Ala Val Pro Gly Met Val Trp Gln Asn Arg Asp Ile Tyr Tyr Gln Gly
                595                 600                 605

Pro Ile Trp Ala Lys Ile Pro His Thr Asp Gly His Phe His Pro Ser
                610                 615                 620

Pro Leu Ile Gly Gly Phe Gly Leu Lys His Pro Pro Pro Gln Ile Phe
625                 630                 635                 640

Ile Lys Asn Thr Pro Val Pro Ala Asn Pro Ala Thr Thr Phe Ser Ser
                645                 650                 655

Thr Pro Val Asn Ser Phe Ile Thr Gln Tyr Ser Thr Gly Gln Val Ser
                660                 665                 670

Val Gln Ile Asp Trp Glu Gln Lys Glu Arg Ser Lys Arg Trp Asn Pro
                675                 680                 685

Glu Val Gln Phe Thr Ser Asn Tyr Gly Gln Gln Asn Ser Leu Leu Trp
                690                 695                 700

Ala Pro Asp Ala Ala Gly Lys Tyr Thr Glu Pro Arg Ala Ile Gly Thr
705                 710                 715                 720

Arg Tyr Leu Thr His His Leu
                725

<210> SEQ ID NO 5
<211> LENGTH: 716
<212> TYPE: PRT
<213> ORGANISM: adeno-associated virus 5

<400> SEQUENCE: 5

Ser Phe Val Asp His Pro Pro Asp Trp Leu Glu Glu Val Gly Glu Gly
1               5                   10                  15

Leu Arg Glu Phe Leu Gly Leu Glu Ala Gly Pro Pro Lys Pro Lys Pro
                20                  25                  30

Asn Gln Gln His Gln Asp Gln Ala Arg Gly Leu Val Leu Pro Gly Tyr
                35                  40                  45

Asn Tyr Leu Gly Pro Gly Asn Gly Leu Asp Arg Gly Glu Pro Val Asn
50                  55                  60

Arg Ala Asp Glu Val Ala Arg Glu His Asp Ile Ser Tyr Asn Glu Gln
65                  70                  75                  80

Leu Glu Ala Gly Asp Asn Pro Tyr Leu Lys Tyr Asn His Ala Asp Ala
                85                  90                  95

Glu Phe Glu Lys Leu Ala Asp Asp Thr Ser Phe Gly Gly Asn Leu Gly
                100                 105                 110

Lys Ala Val Phe Gln Ala Lys Lys Arg Val Leu Glu Pro Phe Gly Leu
                115                 120                 125

Val Glu Glu Gly Ala Lys Thr Ala Pro Thr Gly Lys Arg Ile Asp Asp
                130                 135                 140

His Phe Pro Lys Arg Lys Lys Ala Arg Thr Glu Glu Asp Ser Lys Pro
145                 150                 155                 160

Ser Thr Ser Ser Asp Ala Glu Ala Gly Pro Ser Gly Ser Gln Gln Leu
                165                 170                 175
```

```
Gln Ile Pro Ala Gln Pro Ala Ser Ser Leu Gly Asp Thr Met Ser Ala
                180                 185                 190
Gly Gly Gly Gly Pro Leu Gly Asp Asn Asn Gln Gly Ala Asp Gly Val
            195                 200                 205
Gly Asn Ala Ser Gly Asp Trp His Cys Asp Ser Thr Trp Met Gly Asp
        210                 215                 220
Arg Val Val Thr Lys Ser Thr Arg Thr Trp Val Leu Pro Ser Tyr Asn
225                 230                 235                 240
Asn His Gln Tyr Arg Glu Ile Lys Ser Gly Ser Val Asp Gly Ser Asn
                245                 250                 255
Ala Asn Ala Tyr Phe Gly Tyr Ser Thr Pro Trp Gly Tyr Phe Asp Phe
            260                 265                 270
Asn Arg Phe His Ser His Trp Ser Pro Arg Asp Trp Gln Leu Ile Asn
        275                 280                 285
Asn Tyr Trp Gly Phe Arg Pro Arg Ser Leu Arg Val Lys Ile Phe Asn
        290                 295                 300
Ile Gln Val Lys Glu Val Thr Val Gln Asp Ser Thr Thr Thr Ile Ala
305                 310                 315                 320
Asn Asn Leu Thr Ser Thr Val Gln Val Phe Thr Asp Asp Asp Tyr Gln
                325                 330                 335
Leu Pro Tyr Val Val Gly Asn Gly Thr Glu Gly Cys Leu Pro Ala Phe
            340                 345                 350
Pro Pro Gln Val Phe Thr Leu Pro Gln Tyr Gly Tyr Ala Thr Leu Asn
        355                 360                 365
Arg Asp Asn Thr Glu Asn Pro Thr Glu Arg Ser Ser Phe Phe Cys Glu
370                 375                 380
Tyr Phe Pro Ser Lys Met Leu Arg Thr Gly Asn Asn Phe Glu Phe Thr
385                 390                 395                 400
Tyr Asn Phe Glu Glu Val Pro Phe His Ser Ser Phe Ala Pro Ser Gln
                405                 410                 415
Asn Leu Phe Lys Leu Ala Asn Pro Leu Val Asp Gln Tyr Leu Tyr Arg
            420                 425                 430
Phe Val Ser Thr Asn Asn Thr Gly Gly Val Gln Phe Asn Lys Asn Leu
        435                 440                 445
Ala Gly Arg Tyr Ala Asn Thr Tyr Lys Asn Trp Phe Pro Gly Pro Met
450                 455                 460
Gly Arg Thr Gln Gly Trp Asn Leu Gly Ser Gly Asn Arg Ala Ser Val
465                 470                 475                 480
Ser Ala Phe Ala Thr Thr Asn Arg Met Glu Leu Glu Gly Ala Ser Tyr
                485                 490                 495
Gln Val Pro Pro Gln Pro Asn Gly Met Thr Asn Asn Leu Gln Gly Ser
            500                 505                 510
Asn Thr Tyr Ala Leu Glu Asn Thr Met Ile Phe Asn Ser Gln Pro Ala
        515                 520                 525
Asn Pro Gly Thr Thr Ala Thr Tyr Leu Glu Gly Asn Met Leu Ile Thr
        530                 535                 540
Ser Glu Ser Glu Thr Gln Pro Val Asn Arg Val Ala Tyr Asn Val Gly
545                 550                 555                 560
Gly Gln Met Ala Thr Asn Asn Gln Ser Thr Thr Ala Pro Ala Thr Gly
                565                 570                 575
Thr Tyr Asn Leu Gln Glu Ile Val Pro Gly Ser Val Trp Met Glu Arg
            580                 585                 590
Asp Val Tyr Leu Gln Gly Pro Ile Trp Ala Lys Ile Pro Glu Thr Gly
```

```
                 595                 600                 605
Ala His Phe His Pro Ser Pro Ala Met Gly Gly Phe Gly Leu Lys His
    610                 615                 620

Pro Pro Pro Met Met Leu Ile Lys Asn Thr Pro Val Pro Gly Asn Ile
625                 630                 635                 640

Thr Ser Phe Ser Asp Val Pro Val Ser Ser Phe Ile Thr Gln Tyr Ser
                645                 650                 655

Thr Gly Gln Val Thr Val Glu Met Glu Trp Glu Lys Lys Glu Asn Ser
            660                 665                 670

Lys Arg Trp Asn Pro Glu Ile Gln Tyr Thr Asn Asn Tyr Asn Asp Pro
        675                 680                 685

Gln Phe Val Asp Phe Ala Pro Asp Ser Thr Gly Glu Tyr Arg Thr Thr
    690                 695                 700

Arg Pro Ile Gly Thr Arg Tyr Leu Thr Arg Pro Leu
705                 710                 715

<210> SEQ ID NO 6
<211> LENGTH: 728
<212> TYPE: PRT
<213> ORGANISM: adeno-associated virus 6

<400> SEQUENCE: 6

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Phe Gly
        115                 120                 125

Leu Val Glu Glu Gly Ala Lys Thr Ala Pro Gly Lys Lys Arg Pro Val
    130                 135                 140

Glu Gln Ser Pro Gln Glu Pro Asp Ser Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255
```

-continued

```
Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Leu Ile Asn Asn Asn Trp Gly Phe Arg
    290                 295                 300

Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asn Asn Gly Ser Gln Ala Val
    370                 375                 380

Gly Arg Ser Ser Phe Tyr Cys Glu Tyr Phe Pro Ser Gln Met Leu Arg
385                 390                 395                 400

Thr Gly Asn Asn Phe Thr Phe Ser Tyr Thr Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Asn Arg Thr Gln Asn Gln Ser
        435                 440                 445

Gly Ser Ala Gln Asn Lys Asp Leu Leu Phe Ser Arg Gly Ser Pro Ala
    450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asn Asn Asn Ser Asn Phe Thr
                485                 490                 495

Trp Thr Gly Ala Ser Lys Tyr Asn Leu Asn Gly Arg Glu Ser Ile Ile
            500                 505                 510

Asn Pro Gly Thr Ala Met Ala Ser His Lys Asp Asp Lys Asp Lys Phe
        515                 520                 525

Phe Pro Met Ser Gly Val Met Ile Phe Gly Lys Glu Ser Ala Gly Ala
    530                 535                 540

Ser Asn Thr Ala Leu Asp Asn Val Met Ile Thr Asp Glu Glu Glu Ile
545                 550                 555                 560

Lys Ala Thr Asn Pro Val Ala Thr Glu Arg Phe Gly Thr Val Ala Val
                565                 570                 575

Asn Leu Gln Ser Ser Thr Asp Pro Ala Thr Gly Asp Val His Val Met
            580                 585                 590

Gly Ala Leu Pro Gly Met Val Trp Gln Asp Arg Asp Val Tyr Leu Gln
        595                 600                 605

Gly Pro Ile Trp Ala Lys Ile Pro His Thr Asp Gly His Phe His Pro
    610                 615                 620

Ser Pro Leu Met Gly Gly Phe Gly Leu Lys His Pro Pro Pro Gln Ile
625                 630                 635                 640

Leu Ile Lys Asn Thr Pro Val Pro Ala Asn Pro Pro Ala Glu Phe Ser
                645                 650                 655

Ala Thr Lys Phe Ala Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
```

```
            675                 680                 685
Pro Glu Val Gln Tyr Thr Ser Asn Tyr Ala Lys Ser Ala Asn Val Asp
    690                 695                 700

Phe Thr Val Asp Asn Asn Gly Leu Tyr Thr Glu Pro Arg Pro Ile Gly
705                 710                 715                 720

Thr Arg Tyr Leu Thr Arg Pro Leu
                725

<210> SEQ ID NO 7
<211> LENGTH: 729
<212> TYPE: PRT
<213> ORGANISM: adeno-associated virus 7

<400> SEQUENCE: 7

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
                20                  25                  30

Ala Asn Gln Gln Lys Gln Asp Asn Gly Arg Gly Leu Val Leu Pro Gly
            35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
    115                 120                 125

Leu Val Glu Glu Gly Ala Lys Thr Ala Pro Ala Lys Lys Arg Pro Val
130                 135                 140

Glu Pro Ser Pro Gln Arg Ser Pro Asp Ser Ser Thr Gly Ile Gly Lys
145                 150                 155                 160

Lys Gly Gln Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Ser Ser Val Gly Gly Thr Val Ala Ala Gly Gly Gly Ala Pro
    195                 200                 205

Met Ala Asp Asn Asn Glu Gly Ala Asp Gly Val Gly Asn Ala Ser Gly
210                 215                 220

Asn Trp His Cys Asp Ser Thr Trp Leu Gly Asp Arg Val Ile Thr Thr
225                 230                 235                 240

Ser Thr Arg Thr Trp Ala Leu Pro Thr Tyr Asn Asn His Leu Tyr Lys
                245                 250                 255

Gln Ile Ser Ser Glu Thr Ala Gly Ser Thr Asn Asp Asn Thr Tyr Phe
            260                 265                 270

Gly Tyr Ser Thr Pro Trp Gly Tyr Phe Asp Phe Asn Arg Phe His Cys
    275                 280                 285

His Phe Ser Pro Arg Asp Trp Gln Leu Ile Asn Asn Asn Trp Gly Phe
290                 295                 300

Arg Pro Lys Lys Leu Arg Phe Lys Leu Phe Asn Ile Gln Val Lys Glu
305                 310                 315                 320
```

-continued

```
Val Thr Thr Asn Asp Gly Val Thr Thr Ile Ala Asn Asn Leu Thr Ser
                325                 330                 335
Thr Ile Gln Val Phe Ser Asp Ser Glu Tyr Gln Leu Pro Tyr Val Leu
            340                 345                 350
Gly Ser Ala His Gln Gly Cys Leu Pro Pro Phe Pro Ala Asp Val Phe
        355                 360                 365
Met Ile Pro Gln Tyr Gly Tyr Leu Thr Leu Asn Asn Gly Ser Gln Ser
370                 375                 380
Val Gly Arg Ser Ser Phe Tyr Cys Glu Tyr Phe Pro Ser Gln Met Leu
385                 390                 395                 400
Arg Thr Gly Asn Asn Phe Glu Phe Ser Tyr Ser Phe Glu Asp Val Pro
                405                 410                 415
Phe His Ser Ser Tyr Ala His Ser Gln Ser Leu Asp Arg Leu Met Asn
            420                 425                 430
Pro Leu Ile Asp Gln Tyr Leu Tyr Tyr Leu Ala Arg Thr Gln Ser Asn
        435                 440                 445
Pro Gly Gly Thr Ala Gly Asn Arg Glu Leu Gln Phe Tyr Gln Gly Gly
    450                 455                 460
Pro Ser Thr Met Ala Glu Gln Ala Lys Asn Trp Leu Pro Gly Pro Cys
465                 470                 475                 480
Phe Arg Gln Gln Arg Val Ser Lys Thr Leu Asp Asn Asn Ser Asn
                485                 490                 495
Phe Ala Trp Thr Gly Ala Thr Lys Tyr His Leu Asn Gly Arg Asn Ser
            500                 505                 510
Leu Val Asn Pro Gly Val Ala Met Ala Thr His Lys Asp Asp Glu Asp
        515                 520                 525
Arg Phe Phe Pro Ser Ser Gly Val Leu Ile Phe Gly Lys Thr Gly Ala
    530                 535                 540
Thr Asn Lys Thr Thr Leu Glu Asn Val Leu Met Thr Asn Glu Glu Glu
545                 550                 555                 560
Ile Arg Pro Thr Asn Pro Val Ala Thr Glu Glu Tyr Gly Ile Val Ser
                565                 570                 575
Ser Asn Leu Gln Ala Asn Thr Ala Ala Gln Thr Gln Val Val Asn Asn
            580                 585                 590
Gln Gly Ala Leu Pro Gly Met Val Trp Gln Asn Arg Asp Val Tyr Leu
        595                 600                 605
Gln Gly Pro Ile Trp Ala Lys Ile Pro His Thr Asp Gly Asn Phe His
    610                 615                 620
Pro Ser Pro Leu Met Gly Gly Phe Gly Leu Lys His Pro Pro Gln
625                 630                 635                 640
Ile Leu Ile Lys Asn Thr Pro Val Pro Ala Asn Pro Pro Glu Val Phe
                645                 650                 655
Thr Pro Ala Lys Phe Ala Ser Phe Ile Thr Gln Tyr Ser Thr Gly Gln
            660                 665                 670
Val Ser Val Glu Ile Glu Trp Glu Gln Lys Glu Asn Ser Lys Arg Trp
        675                 680                 685
Asn Pro Glu Ile Gln Tyr Thr Ser Asn Phe Glu Lys Gln Thr Gly Val
    690                 695                 700
Asp Phe Ala Val Asp Ser Gln Gly Val Tyr Ser Glu Pro Arg Pro Ile
705                 710                 715                 720
Gly Thr Arg Tyr Leu Thr Arg Asn Leu
                725
```

<210> SEQ ID NO 8
<211> LENGTH: 730
<212> TYPE: PRT
<213> ORGANISM: adeno-associated virus 8

<400> SEQUENCE: 8

| | | | | | | | | | | | | | | |
|---|---|---|---|---|---|---|---|---|---|---|---|---|---|---|
| Ala | Ala | Asp | Gly | Tyr | Leu | Pro | Asp | Trp | Leu | Glu | Asp | Asn | Leu | Ser | Glu |
| 1 | | | | 5 | | | | | 10 | | | | | 15 | |
| Gly | Ile | Arg | Glu | Trp | Trp | Ala | Leu | Lys | Pro | Gly | Ala | Pro | Lys | Pro | Lys |
| | | | 20 | | | | | 25 | | | | | 30 | | |
| Ala | Asn | Gln | Gln | Lys | Gln | Asp | Asp | Gly | Arg | Gly | Leu | Val | Leu | Pro | Gly |
| | | 35 | | | | | 40 | | | | | 45 | | | |
| Tyr | Lys | Tyr | Leu | Gly | Pro | Phe | Asn | Gly | Leu | Asp | Lys | Gly | Glu | Pro | Val |
| | 50 | | | | | 55 | | | | | 60 | | | | |
| Asn | Ala | Ala | Asp | Ala | Ala | Ala | Leu | Glu | His | Asp | Lys | Ala | Tyr | Asp | Gln |
| 65 | | | | | 70 | | | | | 75 | | | | | 80 |
| Gln | Leu | Gln | Ala | Gly | Asp | Asn | Pro | Tyr | Leu | Arg | Tyr | Asn | His | Ala | Asp |
| | | | | 85 | | | | | 90 | | | | | 95 | |
| Ala | Glu | Phe | Glu | Arg | Leu | Gln | Glu | Asp | Thr | Ser | Phe | Gly | Gly | Asn | Leu |
| | | | 100 | | | | | 105 | | | | | 110 | | |
| Gly | Arg | Ala | Val | Phe | Gln | Ala | Lys | Lys | Arg | Val | Leu | Glu | Pro | Leu | Gly |
| | | | 115 | | | | | 120 | | | | | 125 | | |
| Leu | Val | Glu | Glu | Gly | Ala | Lys | Thr | Ala | Pro | Gly | Lys | Lys | Arg | Pro | Val |
| | 130 | | | | | 135 | | | | | 140 | | | | |
| Glu | Pro | Ser | Pro | Gln | Arg | Ser | Pro | Asp | Ser | Ser | Thr | Gly | Ile | Gly | Lys |
| 145 | | | | | 150 | | | | | 155 | | | | | 160 |
| Lys | Gly | Gln | Gln | Pro | Ala | Arg | Lys | Arg | Leu | Asn | Phe | Gly | Gln | Thr | Gly |
| | | | | 165 | | | | | 170 | | | | | 175 | |
| Asp | Ser | Glu | Ser | Val | Pro | Asp | Pro | Gln | Pro | Leu | Gly | Glu | Pro | Pro | Ala |
| | | | 180 | | | | | 185 | | | | | 190 | | |
| Ala | Pro | Ser | Gly | Val | Gly | Asn | Thr | Met | Ala | Ala | Gly | Gly | Gly | Ala | Pro |
| | | | 195 | | | | | 200 | | | | | 205 | | |
| Met | Ala | Asp | Asn | Asn | Glu | Gly | Ala | Asp | Gly | Val | Gly | Ser | Ser | Ser | Gly |
| | 210 | | | | | 215 | | | | | 220 | | | | |
| Asn | Trp | His | Cys | Asp | Ser | Thr | Trp | Leu | Gly | Asp | Arg | Val | Ile | Thr | Thr |
| 225 | | | | | 230 | | | | | 235 | | | | | 240 |
| Ser | Thr | Arg | Thr | Trp | Ala | Leu | Pro | Thr | Tyr | Asn | Asn | His | Leu | Tyr | Lys |
| | | | | 245 | | | | | 250 | | | | | 255 | |
| Gln | Ile | Ser | Asn | Gly | Thr | Ser | Gly | Gly | Ala | Thr | Asn | Asp | Asn | Thr | Tyr |
| | | | 260 | | | | | 265 | | | | | 270 | | |
| Phe | Gly | Tyr | Ser | Thr | Pro | Trp | Gly | Tyr | Phe | Asp | Phe | Asn | Arg | Phe | His |
| | | | 275 | | | | | 280 | | | | | 285 | | |
| Cys | His | Phe | Ser | Pro | Arg | Asp | Trp | Gln | Leu | Ile | Asn | Asn | Asn | Trp | Gly |
| | 290 | | | | | 295 | | | | | 300 | | | | |
| Phe | Arg | Pro | Lys | Arg | Leu | Ser | Phe | Lys | Leu | Phe | Asn | Ile | Gln | Val | Lys |
| 305 | | | | | 310 | | | | | 315 | | | | | 320 |
| Glu | Val | Thr | Gln | Asn | Glu | Gly | Thr | Lys | Thr | Ile | Ala | Asn | Asn | Leu | Thr |
| | | | | 325 | | | | | 330 | | | | | 335 | |
| Ser | Thr | Ile | Gln | Val | Phe | Thr | Asp | Ser | Glu | Tyr | Gln | Leu | Pro | Tyr | Val |
| | | | 340 | | | | | 345 | | | | | 350 | | |
| Leu | Gly | Ser | Ala | His | Gln | Gly | Cys | Leu | Pro | Pro | Phe | Pro | Ala | Asp | Val |
| | | | 355 | | | | | 360 | | | | | 365 | | |
| Phe | Met | Ile | Pro | Gln | Tyr | Gly | Tyr | Leu | Thr | Leu | Asn | Asn | Gly | Ser | Gln |
| | 370 | | | | | 375 | | | | | 380 | | | | |

-continued

```
Ala Val Gly Arg Ser Ser Phe Tyr Cys Glu Tyr Phe Pro Ser Gln Met
385                 390                 395                 400

Leu Arg Thr Gly Asn Asn Phe Gln Phe Thr Tyr Thr Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Thr
        435                 440                 445

Thr Gly Gly Thr Ala Asn Thr Gln Thr Leu Gly Phe Ser Gln Gly Gly
    450                 455                 460

Pro Asn Thr Met Ala Asn Gln Ala Lys Asn Trp Leu Pro Gly Pro Cys
465                 470                 475                 480

Tyr Arg Gln Gln Arg Val Ser Thr Thr Thr Gly Asn Asn Asn Ser Asn
                485                 490                 495

Phe Ala Trp Thr Ala Gly Thr Lys Tyr His Leu Asn Gly Arg Asn Ser
            500                 505                 510

Leu Ala Asn Pro Gly Ile Ala Met Ala Thr His Lys Asp Asp Glu Glu
        515                 520                 525

Arg Phe Phe Pro Ser Asn Gly Ile Leu Ile Phe Gly Lys Gln Asn Ala
    530                 535                 540

Ala Arg Asp Asn Ala Asp Tyr Ser Asp Val Met Leu Thr Ser Glu Glu
545                 550                 555                 560

Glu Ile Lys Thr Thr Asn Pro Val Ala Thr Glu Tyr Gly Ile Val
                565                 570                 575

Ala Asp Asn Leu Gln Gln Asn Thr Ala Pro Gln Ile Gly Thr Val Asn
            580                 585                 590

Ser Gln Gly Ala Leu Pro Gly Met Val Trp Gln Asn Arg Asp Val Tyr
        595                 600                 605

Leu Gln Gly Pro Ile Trp Ala Lys Ile Pro His Thr Asp Gly Asn Phe
    610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
                645                 650                 655

Phe Asn Gln Ser Lys Leu Asn Ser Phe Ile Thr Gln Tyr Ser Thr Gly
            660                 665                 670

Gln Val Ser Val Glu Ile Glu Trp Glu Leu Gln Lys Glu Asn Ser Lys Arg
        675                 680                 685

Trp Asn Pro Glu Ile Gln Tyr Thr Ser Asn Tyr Lys Ser Thr Ser
    690                 695                 700

Val Asp Phe Ala Val Asn Thr Glu Gly Val Tyr Ser Glu Pro Arg Pro
705                 710                 715                 720

Ile Gly Thr Arg Tyr Leu Thr Arg Asn Leu
                725                 730
```

<210> SEQ ID NO 9
<211> LENGTH: 728
<212> TYPE: PRT
<213> ORGANISM: adeno-associated virus 9

<400> SEQUENCE: 9

```
Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Ala Pro Gln Pro Lys
            20                  25                  30
```

```
Ala Asn Gln Gln His Gln Asp Asn Ala Arg Gly Leu Val Leu Pro Gly
         35                  40                  45

Tyr Lys Tyr Leu Gly Pro Gly Asn Gly Leu Asp Lys Gly Glu Pro Val
 50                  55                  60

Asn Ala Ala Asp Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Glu Arg Leu Lys Glu Asp Thr Ser Phe Gly Gly Asn Leu
             100                 105                 110

Gly Arg Ala Val Phe Gln Ala Lys Lys Arg Leu Leu Glu Pro Leu Gly
         115                 120                 125

Leu Val Glu Glu Ala Ala Lys Thr Ala Pro Gly Lys Lys Arg Pro Val
130                 135                 140

Glu Gln Ser Pro Gln Glu Pro Asp Ser Ser Ala Gly Ile Gly Lys Ser
145                 150                 155                 160

Gly Ala Gln Pro Ala Lys Lys Arg Leu Asn Phe Gly Gln Thr Gly Asp
                 165                 170                 175

Thr Glu Ser Val Pro Asp Pro Gln Pro Ile Gly Glu Pro Pro Ala Ala
             180                 185                 190

Pro Ser Gly Val Gly Leu Thr Met Ala Ser Gly Gly Ala Pro Val
         195                 200                 205

Ala Asp Asn Asn Glu Gly Ala Asp Gly Val Gly Ser Ser Ser Gly Asn
210                 215                 220

Trp His Cys Asp Ser Gln Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                 245                 250                 255

Ile Ser Asn Ser Thr Ser Gly Gly Ser Ser Asn Asp Asn Ala Tyr Phe
             260                 265                 270

Gly Tyr Ser Thr Pro Trp Gly Tyr Phe Asp Phe Asn Arg Phe His Cys
         275                 280                 285

His Phe Ser Pro Arg Asp Trp Gln Leu Ile Asn Asn Trp Gly Phe
         290                 295                 300

Arg Pro Lys Arg Leu Asn Phe Lys Leu Phe Asn Ile Gln Val Lys Glu
305                 310                 315                 320

Val Thr Asp Asn Asn Gly Val Lys Thr Ile Ala Asn Asn Leu Thr Ser
                 325                 330                 335

Thr Val Gln Val Phe Thr Asp Ser Asp Tyr Gln Leu Pro Tyr Val Leu
             340                 345                 350

Gly Ser Ala His Glu Gly Cys Leu Pro Pro Phe Pro Ala Asp Val Phe
         355                 360                 365

Met Ile Pro Gln Tyr Gly Tyr Leu Thr Leu Asn Asp Gly Ser Gln Ala
370                 375                 380

Val Gly Arg Ser Ser Phe Tyr Cys Glu Tyr Phe Pro Ser Gln Met Leu
385                 390                 395                 400

Arg Thr Gly Asn Asn Phe Gln Phe Ser Tyr Glu Phe Glu Asn Val Pro
                 405                 410                 415

Phe His Ser Ser Tyr Ala His Ser Gln Ser Leu Asp Arg Leu Met Asn
             420                 425                 430

Pro Leu Ile Asp Gln Tyr Leu Tyr Tyr Leu Ser Lys Thr Ile Asn Gly
         435                 440                 445
```

```
Ser Gly Gln Asn Gln Gln Thr Leu Lys Phe Ser Val Ala Gly Pro Ser
    450                 455                 460

Asn Met Ala Val Gln Gly Arg Asn Tyr Ile Pro Gly Pro Ser Tyr Arg
465                 470                 475                 480

Gln Gln Arg Val Ser Thr Thr Val Thr Asn Asn Asn Ser Glu Phe Ala
                485                 490                 495

Trp Pro Gly Ala Ser Ser Trp Ala Leu Asn Gly Arg Asn Ser Leu Met
                500                 505                 510

Asn Pro Gly Pro Ala Met Ala Ser His Lys Glu Gly Glu Asp Arg Phe
            515                 520                 525

Phe Pro Leu Ser Gly Ser Leu Ile Phe Gly Lys Gln Gly Thr Gly Arg
530                 535                 540

Asp Asn Val Asp Ala Asp Lys Val Met Ile Thr Asn Glu Glu Glu Ile
545                 550                 555                 560

Lys Thr Thr Asn Pro Val Ala Thr Glu Ser Tyr Gly Gln Val Ala Thr
                565                 570                 575

Asn His Gln Ser Gln Ala Gln Ala Gln Thr Gly Trp Val Gln Asn Gln
            580                 585                 590

Gly Ile Leu Pro Gly Met Val Trp Gln Asp Arg Asp Val Tyr Leu Gln
        595                 600                 605

Gly Pro Ile Trp Ala Lys Ile Pro His Thr Asp Gly Asn Phe His Pro
    610                 615                 620

Ser Pro Leu Met Gly Gly Phe Gly Met Lys His Pro Pro Gln Ile
625                 630                 635                 640

Leu Ile Lys Asn Thr Pro Val Pro Ala Asp Pro Pro Thr Ala Phe Asn
                645                 650                 655

Lys Asp Lys Leu Asn Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
        675                 680                 685

Pro Glu Ile Gln Tyr Thr Ser Asn Tyr Tyr Lys Ser Asn Asn Val Glu
    690                 695                 700

Phe Ala Val Asn Thr Glu Gly Val Tyr Ser Glu Pro Arg Pro Ile Gly
705                 710                 715                 720

Thr Arg Tyr Leu Thr Arg Asn Leu
                725

<210> SEQ ID NO 10
<211> LENGTH: 738
<212> TYPE: PRT
<213> ORGANISM: adeno-associated virus 10

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

-continued

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
        115                 120                 125

Leu Gly Leu Val Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
                195                 200                 205

Gly Ala Pro Met Ala Asp Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
        500                 505                 510

-continued

```
Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

RAAV VECTOR COMPOSITIONS, METHODS FOR TARGETING VASCULAR ENDOTHELIAL CELLS AND USE IN TREATMENT OF TYPE I DIABETES

CROSS-REFERENCE TO RELATED APPLICATIONS

The present application is a national stage filing under 35 U.S.C. § 371 of International Application Number PCT/US2016/018098, filed Feb. 16, 2016, which claims priority to U.S. Provisional Patent Application No. 62/116,863, filed Feb. 16, 2015, the contents of each of which are specifically incorporated herein in their entirety.

STATEMENT REGARDING FEDERALLY SPONSORED RESEARCH OR DEVELOPMENT

This invention was made with government support under grant number EY021721 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present disclosure relates generally to the fields of molecular biology and virology, and in particular, to the development of gene delivery vehicles. Disclosed are improved recombinant adeno-associated viral (rAAV) vector compositions useful in delivering a variety of nucleic acid segments, including those encoding diagnostic or therapeutic proteins polypeptides, peptides, antisense oligonucleotides, and ribozyme constructs to selected host cells for use in various diagnostic and/or therapeutic regimens. Methods are also provided for preparing and using these modified rAAV-based vector constructs in a variety of viral-based gene therapies, and in particular, for the diagnosis, prevention, treatment and/or amelioration of symptoms of inflammation, vascular complications from diabetes such as retinopathy, nephropathy, atherosclerotic plaque formation, reduced myocardial perfusion, and reduced wound healing, as well as underlying defects in one or more components of the mammalian vascular system. The invention also provides multi-capsid-mutated rAAV-based viral vector expression systems that show marked increased in transduction efficiency and/or improved viral infectivity of mammalian vascular endothelial cells (VECs). In particular, the invention provides novel AAV capsid mutant/cellular promoter combinations that, when administered to mammals, are capable of selectively driving transgene expression in VECs.

Description of Related Art

Major advances in the field of gene therapy have been achieved by using viruses to deliver therapeutic genetic material. AAV has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, rAAV DNA is packaged into the viral capsid as a single-stranded molecule about 4600-nucleotides (nt) in length. Following infection of the cell by the virus, the molecular machinery of the cell converts the single-stranded (ss) DNA into a double-stranded (ds) form. Only this dsDNA form is able to be transcribed by cellular enzymes into RNA, which is then translated into polypeptides by additional cellular pathways.

AAV vectors have many properties that favor their use as gene delivery vehicles in mammalian hosts: 1) the wild-type (wt) virus is not associated with any pathologic human condition; 2) the recombinant form does not contain native viral coding sequences; and 3) persistent transgenic expression has been observed in a variety of mammalian cells, facilitating their use in many gene therapy-based applications.

The transduction efficiency of serotype 2 vectors (rAAV2) varies greatly in different cells and tissues in vitro and in vivo, and that fact limits their usefulness in certain gene therapy regimens. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro as well as in vivo.

It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids.

Deficiencies in the Prior Art

What is lacking in the prior art are improved rAAV viral vectors that have enhanced transduction efficiency for infecting selected mammalian cells, and for targeted gene expression in human VECs in particular.

BRIEF SUMMARY OF THE INVENTION

The present disclosure overcomes these and other limitations in the prior art by providing rAAV-based expression systems for efficiently transducing mammalian VECs. The system relies on the use of particular promoters that, when used to express genes of interest, and when packaged in capsid-protein-modified AAV virions, can be used to efficiently transform target mammalian cells, and effectively drive transgene expression in transformed VECs. It is contemplated that human gene therapy will particularly benefit from these new viral vector constructs for use in the treatment of a number of diverse diseases, disorders, and dysfunctions involving VECs and disorders of the mammalian vascular system.

Exemplary synthetic VEC-targeting promoters have been derived in part from the human VE-cadherin control region, and combined with other regulatory sequences to produce expression cassettes capable of expressing selected diagnostic and/or therapeutic molecules of interest in a reproducible, biologically-effective manner, over sustained periods following administration in mammalian hosts.

In exemplary embodiments, a pentuple-mutated rAAV capsid variant has been constructed, and was used to package expression cassettes that contain VEC-specific promoters operably linked to one or more diagnostic or therapeutic molecules. When administered to mammalian subjects, these expression constructs efficiently and selectively transduced VECs, both in vitro and in vivo, at very high efficiencies.

Importantly, the vectors disclosed herein provide a platform technology for overcoming dysfunction in the retinal vascular endothelium, which is often associated with an underlying condition such as diabetes mellitus (i.e., diabetic retinopathy). Moreover, the results presented herein extend their applicability to even broader treatment regimens, since VECs play a pivotal role in the pathophysiology of a multitude of diseases, including, for example, hypercholesterolemia, inflammation, and vasculitis. Because endothelial impairment is a hallmark of coronary artery disease, hypertension, and atherosclerosis, the ability to selectively express particular therapeutics in VECs to a high degree of efficiency and specificity using the disclosed compositions and methods, opens the door to a whole suite of interventional approaches that were heretofore unavailable for treatment of these and other complex, multifactorial diseases.

The improved rAAV vectors disclosed herein preferably transduce mammalian VECs at higher-efficiencies (and often, much higher efficiencies) than conventional, wild-type unmodified rAAV vector constructs. By employing multi-mutated capsid protein-encoding rAAV vectors (including those having combinations of five or more surface-exposed amino acid residues), multi-mutated rAAV expression constructs have been developed that can package expression cassettes containing vascular endothelial cell-specific promoters operably linked to a selected nucleic acid segment that expresses or encodes a therapeutic or diagnostic agent of interest in transformed VECs.

In exemplary embodiments, an expression cassette encoding the human GTP cyclohydrolase protein operably linked to a truncated human VE-cadherin promoter sequence was created that, when packaged by the pentuple capsid mutant virions, efficiently transformed human VECs and expressed the protein in therapeutic levels.

The novel expression systems described herein offer improved properties and afford higher-efficiency transduction than compared to the corresponding, non-substituted (i.e., un-modified) parent vectors from which the mutants were prepared.

In a particular embodiment the invention provides improved rAAV capsid-modified vectors that have been derived from a number of different serotypes, including, for example, but not limited to, those selected from the group consisting of AAV1, AAV2, AAV3, AAV4, AAV5, AAV6, AAV7, AAV8, AAV9, and AAV10, whose capsid protein sequences are set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, respectively.

The invention also provides an isolated and purified polynucleotide that encodes one or more of the disclosed rAAV vectors described herein, as well as pluralities of infectious adeno-associated viral virions that contain such a polynucleotide. Preferably, the vector constructs disclosed herein further include at least one nucleic acid segment that encodes at least one therapeutic agent operably linked to VEC-specific promoter that is capable of expressing the nucleic acid segment in suitable VECs that have been transformed with the vector construct.

In the practice of the present disclosure, the transduction efficiency of a virion comprising a multi-mutated, capsid protein-modified rAAV vector system will be higher than that of the corresponding, unmodified, wild-type protein, and as such, will preferably possess a transduction efficiency in mammalian VECs that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, capsid protein.

In certain embodiments, the transduction efficiency of the rAAV vectors provided herein will be at least about 15-fold higher, at least about 20-fold higher, at least about 25-fold higher, at least about 30-fold higher, or at least about 40, 45, or 50-fold or more greater than that of a virion that comprises a corresponding, unmodified, capsid protein.

The present disclosure also concerns rAAV vectors, wherein the nucleic acid segment further comprises a promoter, an enhancer, a post-transcriptional regulatory sequence, a polyadenylation signal, or any combination thereof, operably linked to the nucleic acid segment that encodes the selected polynucleotide of interest.

Preferably, the promoter is a heterologous promoter, and in particular, a mammalian VEC-specific promoter such as the shortened human VE-cadherin promoter described herein.

As noted herein, the therapeutic agents useful in the invention may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The rAAV vectors of the present disclosure may be packaged into virions of any suitable serotype, including a serotype that is selected from the group consisting of AAV serotype 1, AAV serotype 2, AAV serotype 3, AAV serotype 4, AAV serotype 5, AAV serotype 6, AAV serotype 7, AAV serotype 8, AAV serotype 9, or AAV serotype 10, or any other serotype as known to one of ordinary skill in the viral arts, as well as combinations and chimeras thereof.

In related embodiments, the present disclosure further provides populations and pluralities of rAAV vectors, virions, infectious viral particles, or host cells that include one or more nucleic acid segments that encode an rAAV vector comprising a multi-mutated VP3 protein that includes a VEC-specific promoter operably linked to a selected polynucleotide encoding a therapeutic agent such as GTP cyclohydrolase (GCH1).

The present disclosure also provides composition and formulations that include one or more of the proteins, nucleic acid segments, viral vectors, host cells, or viral particles disclosed herein, together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction, and in particular, for delivery of a therapeutic agent to VECs of a mammal, including, for examples, the vasculature and microvasculature of the human retina.

The present disclosure further includes a method for providing a mammal in need thereof with a diagnostically- or therapeutically-effective amount of a selected diagnostic or therapeutic agent, the method comprising providing to a cell, tissue or organ of a mammal in need thereof, an amount of one or more of the disclosed rAAV multi-capsid mutant vectors; and for a time effective to provide the mammal with a diagnostically- or a therapeutically-effective amount of a selected diagnostic or therapeutic agent.

The invention further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV vectors, in an amount and for a time sufficient to diagnose, prevent, treat or ameliorate the one or more symptoms of the disease, disorder, dysfunction, injury, abnormal condition, or trauma in the mammal.

The invention also provides a method of transducing a population of mammalian cells. In an overall and general sense, the method includes at least the step of introducing into one or more cells of the population, a composition that comprises an effective amount of one or more of the rAAV vectors disclosed herein, wherein the vector encodes one or more diagnostic or therapeutic molecules useful in the treatment, diagnosis, and/or prophylaxis of one or more VEC disorders in a mammal.

In a further embodiment, the invention also provides isolated nucleic acid segments that encode one or more of the AAV mutant capsid proteins as described herein, and provides recombinant vectors, virus particles, infectious virions, and isolated host cells that can package the isolated expression cassettes described herein that contain a VEC-specific promoter operably linked to one or more therapeutic and/or diagnostic molecules of interest.

Additionally, the present disclosure provides compositions, as well as therapeutic and/or diagnostic kits that include one or more of the disclosed rAAV vector compositions, formulated with one or more additional ingredients, or prepared with one or more instructions for their use in one or more diagnostic or therapeutic regimens.

The present disclosure also provides methods for making, as well as methods of using, the disclosed improved rAAV capsid-mutated vectors in a variety of ways, including, for example, ex situ, in vitro and in vivo applications, diagnostic regimens, and gene therapy treatment modalities. Because many of the improved vectors described herein are resistant to proteasomal degradation, they possess significantly increased transduction efficiencies in vivo making them particularly suited for viral vector-based human gene therapy regimens, and for delivering one or more genetic constructs to selected mammalian cells in vivo and/or in vitro.

In one aspect, the present disclosure also provides compositions that include rAAV vectors, virions, viral particles, and pharmaceutical formulations thereof, useful in methods for delivering genetic material encoding one or more beneficial or therapeutic product(s) to mammalian VECs, as well as tissues and/or organs containing one or more VECs. In particular, the compositions and methods of the invention provide a significant advancement in the art through their use in the treatment, prevention, and/or amelioration of symptoms of one or more mammalian VEC-related diseases, including those arising from complications due to underlying Type I diabetes, hypertension, artherosclerosis, hypercholesterolemia, inflammation, and related diseases.

In another aspect, the present disclosure provides modified rAAV vectors that encode one or more mammalian therapeutic agents for the prevention, treatment, and/or amelioration of one or more disorders in the mammal into which the vector construct is delivered.

In certain embodiments, the present disclosure provides rAAV-based expression constructs that encode one or more mammalian therapeutic agent(s) (including, but not limited to, one or more protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, defect, diorder, deficiency, injury, or trauma.

The surface-exposed amino acid-modified rAAV vectors disclosed herein preferably include one or more promoter sequences that are each operably linked to the nucleic acid segment of interest. Exemplary promoters useful in the practice of the invention include, without limitation, one or more tissue-specific promoters, including, for example, but not limited to, a human VE-cadherin-derived promoter.

The surface-exposed amino acid-modified rAAV vectors disclosed herein may optionally further include one or more enhancer sequences that are each operably linked to the nucleic acid segment of interest. Exemplary enhancer sequences include, but are not limited to, one or more selected from the group consisting of a CMV enhancer, a synthetic enhancer, a vascular-specific enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

The rAAV vectors disclosed herein may also optionally further include one or more post-transcriptional regulatory sequences or one or more polyadenylation signals operably linked to the nucleic acid segment of interest. Such regulatory sequences may include, for example, but are not limited to, a woodchuck hepatitis virus post-transcription regulatory element, a polyadenylation signal sequence, intron/exon junctions/splicing signals, or any combination thereof.

In exemplary embodiments, the rAAV vectors disclosed herein find particular utility when they comprise one or more nucleic acid segments that encode a therapeutic protein or polypeptide such as a photosensitive opsin (including, without limitation, rhodopsin, melanopsin, cone opsins, channel rhodopsins, bacterial or archea-associated opsins), an adrenergic agonist, an anti-apoptosis factor, an apoptosis inhibitor, a cyclohydrolase, a cytokine receptor, a cytokine, a cytotoxin, an erythropoietic agent, a glutamic acid decarboxylase, a glycoprotein, a growth factor, a growth factor receptor, a hormone, a hormone receptor, a hydrolase, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

The exogenous polynucleotide(s) that may be delivered into host cells by the disclosed capsid-modified viral vectors may, in certain embodiments, may express one or more siRNAs, ribozymes, antisense oligonucleotides, PNA molecules, or any combination thereof.

When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a distinct therapeutic agent.

In other embodiments, the invention also provides capsid-modified rAAV vectors that are comprised within an infectious adeno-associated viral particle or a virion, as well as pluralities of such virions or infectious particles. Such vectors and virions may be comprised within one or more diluents, buffers, physiological solutions, or pharmaceutical vehicles, or formulated for administration to a mammal in one or more diagnostic, therapeutic, and/or prophylactic regimens. The vectors, virus particles, virions, and pluralities thereof as disclosed herein may also be provided in excipient formulations that are acceptable for veterinary administration to selected livestock, exotics, domesticated animals, and companion animals (including pets and such like), as well as to non-human primates, zoological or otherwise captive specimens, and such like.

The invention also concerns host cells that comprise at least one of the disclosed capsid protein-modified rAAV expression vectors, or one or more virus particles or virions that comprise such an expression vector. Such host cells are particularly mammalian host cells, with human VECs being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. One significant advantage of the present methods is the ability to utilize lower titers of viral particles in mammalian transduction protocols, yet still retain transfection rates at a suitable level.

Compositions comprising one or more of the disclosed capsid-modified, improved transduction-efficiency rAAV vectors, expression systems, infectious AAV particles, or host cells also form part of the present disclosure, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex.

Alternatively, the surface exposed amino acid-substituted rAAV vectors of the present disclosure may be comprised within a plurality of microspheres, nanoparticles, liposomes, or any combination thereof. Pharmaceutical formulations suitable for systemic administration to a human or other mammal are particularly preferred, however, the compositions disclosed herein may also find utility in administration to discreet or localized areas of the mammalian body, including for example, formulations that are suitable for direct injection (e.g., by direct cannulation) into one or more organs, tissues, or vessels within the body. In certain aspects, localized delivery of the therapeutic constructs may be achieved by temporary vascular occlusion or other inhibition of circulation following direct tissue or direct organ administration, or by cannulation to one or more specific vessels within the body.

Other aspects of the invention concern recombinant adeno-associated virus virion particles, compositions, and host cells that comprise, consist essentially of, or consist of, one or more of the capsid-modified, improved transduction efficiency, rAAV vectors disclosed herein, such as for example pharmaceutical formulations of the vectors intended for intravitreal administration to a mammal in need thereof.

Kits comprising one or more of the disclosed capsid-modified rAAV vector expression systems (as well as one or more virions, viral particles, transformed host cells or pharmaceutical compositions comprising such vectors); and instructions for using such kits in one or more therapeutic, diagnostic, and/or prophylactic clinical embodiments are also provided by the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present disclosure concerns methods of use of the disclosed rAAV vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in the vascular system of a vertebrate mammal. Such methods generally involve systemic or localized administration to a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more therapeutic proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present disclosure, and particularly those compositions that further comprise at least a first pharmaceutically-acceptable excipient for use in the manufacture of medicaments and methods involving therapeutic administration of such rAAV vectors. Pharmaceutical formulations suitable for intravitreal administration into one or both eyes of a human or other mammal are particularly preferred.

Another important aspect of the present disclosure concerns methods of use of the disclosed vectors, virions, expression systems, compositions, and host cells described herein in the preparation of medicaments for treating or ameliorating the symptoms of various deficiencies in an eye of a mammal, and in particular one or more deficiencies in human vasculature. Such methods generally involve administration to a subject in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present disclosure. Should the application contain one or more drawings executed in color, copies of this patent or patent application publication with color drawing(s) will be provided by the United States Patent and Trademark Office upon request and upon payment of the required fee. The invention may be better understood by reference to the following description taken in conjunction with the accompanying drawings, in which like reference numerals identify like elements, and in which:

FIG. 2A, FIG. 2B, and FIG. 2C illustrate transduction of retinal vasculature by an exemplary vector AAV2(quadYF+T-V)-smVECad-GFP, in accordance with one aspect of the present disclosure;

FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L show the in vitro transduction of primary retinal vascular endothelial cells by exemplary AAV2-based capsid mutant vectors in accordance with one aspect of the present disclosure. FIG. 3A, FIG. 3B, FIG. 3C, FIG. 3D, and FIG. 3E show expression of green fluorescent protein (GFP) in primary retinal vascular endothelial cells following transduction with unmodified AAV2 (FIG. 3A), TripleYF (FIG. 3B), TripleYF+T491V (FIG. 3C), QuadYF (FIG. 3D) and QuadYF+T491V (FIG. 3E; see Table 1 for nomenclature) demonstrating increased levels of transduction with multiple capsid mutant vectors over unmodified AAV2. FIG. 3F, FIG. 3G, FIG. 3H, FIG. 3I, FIG. 3J, and FIG. 3K show the quantification of GFP-positive endothelial cells by flow cytometry, comparing AAV2 (FIG. 3F, FIG. 3G, and FIG. 3H) with QuadYF+T491V (FIG. 3I, FIG. 3J, and FIG. 3K) three days post transduction. FIG. 3L shows the quantification of endothelial cell transduction by flow cytometry demonstrating that QuadYF+T491V was significantly more effective than the other vectors examined; ***=$p<0.001$, n=3 per group two-way ANOVA with Bonferroni post-test;

FIG. 4A shows the longitudinal section through a kidney demonstrating GFP expression in the vessel walls of the arcuate artery (1) and vein (2). Section through the liver, showing high levels of GFP fluorescence around the hepatic artery (3) and portal vein (4). Section through the optic disk demonstrating diffuse GFP expression throughout the optic nerve (5); intense GFP expression can be observed in the wall of a central retina vessel (6). Although the choroid of the eye is heavily pigmented, GFP expression can also be observed throughout the choriocapillaries. All images: green=anti-GFP; blue=DAPI;

FIG. 5A shows unmodified AAV2 was effectively neutralized by pre-incubation with primate serum containing high levels of AAV2 neutralizing antibodies (Sero+ve) but not by serum with low levels of AAV2 neutralizing antibodies (Sero−ve). FIG. 5B shows QuadYF+T491V was neutralized to a greater extent by Sero+ve and Sero−ve primate sera than unmodified AAV2, though not significantly (n=3 wells per dilution);

FIG. 6A, FIG. 6B, FIG. 6C, FIG. 6D, and FIG. 6E show the expression of AAV vector mediated GFP in vitro and in vivo. Transduction of primary bovine retinal endothelial cells demonstrated significantly enhanced transduction using an AAV2-derived serotype with five capsid mutations (FIG. 6A) compared to the unmodified AAV2 serotype (FIG. 6B). IV delivery of capsid mutant vector (5 M.smVECad-GFP) resulted in robust in vivo transduction of the retinal vasculature (FIG. 6C). Scale bars=100 μm. Subsets of the image in FIG. 6C are shown in FIG. 6D, and FIG. 6E, respectively.

BRIEF DESCRIPTION OF DISCLOSED AMINO ACID AND/OR NUCLEOTIDE SEQUENCES

Figure 1A:
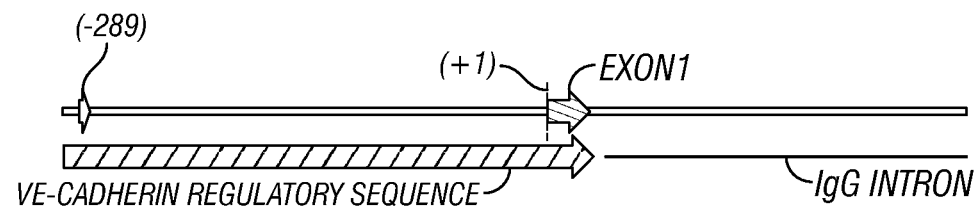
FIG. 1A and FIG. 1B show exemplary chimeric VEC targeting promoters, smVEcad and CMV-seVEcad, respectively in accordance with one aspect of the present disclosure. NB, figures are not to scale.

SEQ ID NO:1 is an amino acid sequence of the capsid protein of the wild-type adeno-associated virus serotype 1 (AAV1);

SEQ ID NO:2 is an amino acid sequence of the capsid protein of the wild-type adeno-associated virus serotype 2 (AAV2);

SEQ ID NO:3 is an amino acid sequence of the capsid protein of the wild-type adeno-associated virus serotype 3 (AAV3);

SEQ ID NO:4 is an amino acid sequence of the capsid protein of the wild-type adeno-associated virus serotype 4 (AAV4);

SEQ ID NO:5 is an amino acid sequence of the capsid protein of the wild-type adeno-associated virus serotype 5 (AAV5);

SEQ ID NO:6 is an amino acid sequence of the capsid protein of the wild-type adeno-associated virus serotype 6 (AAV6);

SEQ ID NO:7 is an amino acid sequence of the capsid protein of the wild-type adeno-associated virus serotype 7 (AAV7);

SEQ ID NO:8 is an amino acid sequence of the capsid protein of the wild-type adeno-associated virus serotype 8 (AAV8);

SEQ ID NO:9 is an amino acid sequence of the capsid protein of the wild-type adeno-associated virus serotype 9 (AAV9); and SEQ ID NO:10 is an amino acid sequence of the capsid protein of the wild-type adeno-associated virus serotype 10 (AAV10).

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

"AAV2(QuadY-F+T-V)" is a pentuple capsid protein mutant that is derived from AAV serotype 2, in which four surface-exposed tyrosine (Y) residues are each mutated to a phenylalanine (F) residue (i.e., "tyrosine-to-phenylalanine" or "Y→F" mutations), and one surface-exposed threonine (T) residue is also mutated to a valine (V) residue (i.e., "threonine-to-valine" or a "T→V" mutation). Specifically, the four mutated tyrosine residues correspond to amino acid positions Tyr272, Tyr 444, Tyr500, and Tyr730 in the AAV2 capsid sequence, and the mutated threonine resides corresponds to amino acid position Thr491 in the AAV2 wild-type sequence. Mutation of the four Y→F and one T→V residues yields the quintuple mutation, (shorthand designation: "Y272F+Y444F+Y500F+Y730F+T491V). Alternatively, the vector is denoted interchangeably herein as "AAV2 (QuadY→F+T→V)" or "AAV2(QuadY→F+T491V)."

rAAV Vectors

Recombinant adeno-associated virus (AAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, i.e., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and $CD8^+$ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007). These results suggested that immune responses remain a concern for AAV vector-mediated gene transfer.

Adeno-associated virus (AAV) is considered the optimal vector for ocular gene therapy due to its efficiency, persistence and low immunogenicity (Daya and Berns, 2008). Identifying vectors capable of transducing PRs via the vitreous will rely partially on identifying which serotypes have native tropism for this cell type following local delivery. Several serotypes have been used to successfully target transgene to PRs following subretinal injection (including, e.g., AAV2, AAV5 and AAV8) with all three demonstrating efficacy in proof of concept experiments across multiple species (e.g., mouse, rat, dog, pig and non-human primate) (Ali et al., 1996; Auricchio et al., 2001; Weber et al., 2003; Yang et al., 2002; Acland et al., 2001; Vandenberghe et al., 2011; Bennett et al., 1999; Allocca et al., 2007; Petersen-Jones et al., 2009; Lotery et al., 2003; Boye et al., 2012; Stieger et al., 2008; Mussolino et al., 2011; Vandenberghe et al., 2011).

Uses for Improved, Capsid-Modified rAAV Vectors

The present disclosure provides compositions including one or more of the disclosed surface exposed amino acid capsid-modified rAAV vectors comprised within a kit for diagnosing, preventing, treating or ameliorating one or more symptoms of a mammalian disease, injury, disorder, defect, deficiency, trauma or dysfunction. Such kits may be useful in diagnosis, prophylaxis, and/or therapy, and particularly useful in the treatment, prevention, and/or amelioration of one or more defects in the mammalian vascular system as discussed herein. The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of a disease, disorder or dysfunction involving vascular endothelial cells, or tissues or organs containing one or more such cells.

Likewise, the invention also provides a method for treating or ameliorating the symptoms of such a disease, injury, disorder, or dysfunction in vascular endothelial cells of a mammal, and of such conditions in a human patient in particular. Such methods generally involve at least the step of administering to a mammal in need thereof, one of the rAAV expression systems as disclosed herein, in an amount and for a time sufficient to treat or ameliorate the symptoms of such a disease, injury, disorder, or dysfunction in the mammal.

Also provided herein is a method for providing to a mammal in need thereof, a therapeutically-effective amount of an rAAV vector composition, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, (or an antigen-binding fragment thereof), a ribozyme, a peptide nucleic acid, an siRNA, an RNAi, an antisense oligonucleotide, an antisense polynucleotide and any combination thereof. Alternatively, the vector constructs may be used to direct or facilitate the expression of one or more diagnostic or "reporter" molecules in selected mammalian cells (either in vitro or in vivo), and in such circumstances, a diagnostic agent, marker, chromogenic agent, fluorogenic molecule, a reporter protein, a detectable compound, or a labeled molecule may be employed in the construction of the expression cassettes described herein.

Pharmaceutical Compositions Comprising rAAV Vectors

One important aspect of the present methodology is the fact that the improved rAAV vectors described herein permit the delivery of smaller titers of viral particles in order to achieve the same transduction efficiency as that obtained using higher levels of conventional, non-surface capsid-modified rAAV vectors. To that end, the amount of rAAV compositions and time of administration of such compositions will be within the purview of the skilled artisan having benefit of the present teachings. In fact, administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or over a relatively prolonged period, as may be determined by the medical practitioner overseeing the administration of such compositions. For example, the number of infectious particles administered to a mammal may be approximately $10^7$, $10^8$, $10^9$, $10^{10}$, $10^{11}$, $10^{12}$, $10^{13}$, or even higher, infectious particles/mL, given either as a single dose (or divided into two or more administrations, etc.) as may be required to achieve therapy of the particular vascular disease or the VEC-related disorder/condition being treated.

In fact, in certain embodiments, it may be desirable to administer two or more different rAAV vector-based compositions, either alone, or in combination with one or more other diagnostic agents, drugs, bioactives, or such like, to achieve the desired effects of a particular regimen or therapy. In most rAAV-vectored, gene therapy-based regimens, lower titers of infectious particles will be required when using the modified-capsid rAAV vectors described herein, as compared to the use of equivalent wild-type, or corresponding "un-modified" rAAV vectors, particularly in the transformation of vascular endothelial cells, and the delivery of therapeutic constructs to selected tissues, organs, or systems, to treat one or more abnormal conditions of vascular endothelial cells in humans in vivo.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present disclosure, one may prepare a capsid-modified rAAV expression vector (e.g., a multi-tyrosine mutated vector) that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise a capsid-protein modified rAAV vector that contains a VEC-specific promoter operably linked to a nucleic acid segment encoding one or more ocular therapeutic agents. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the pentuple-capsid-modified rAAV vectors disclosed herein to package and deliver one or more exogenous polynucleotides to selected host cells, and preferably, to one or more selected host cells within or about the body of a mammal, such as a human. In particular applications, the disclosed constructs are used to package expression cassettes encoding therapeutic polypeptides selected for their ability to treat one or more diseases involving VECs. In exemplary constructs, GTP cyclohydrolase has been expressed under the control of a truncated (shortened) VE-cadherin promoter, with delivery to mammalian cells (either systemically or by localized administration), at very high transduction efficiencies, due to the multi-surface amino acid residue-modified capsid virions into which the expression cassettes were packaged and used to transform the target mammalian cells.

The genetic constructs disclosed herein may be prepared in a variety of compositions, and may also be formulated in appropriate pharmaceutical vehicles for administration to human or animal subjects. The rAAV-vector based expression constructs disclosed herein (as well as compositions and pharmaceutical formulations including them) represent new and useful agents for the diagnosis, prophylaxis, treatment, and/or amelioration of symptoms of one or more disorders, diseases, defects, deficiencies, dysfunctions, injury, and/or trauma of a mammal, and in particular, the human vasculature, vascular endothelial cells, and a host of related complications often arising from underlying Type I diabetes.

Exemplary Definitions

In accordance with the present disclosure, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. The following references provide one of skill with a general definition of many of the terms used in this invention: Singleton et al., *Dictionary of Microbiology and Molecular Biology* (2$^{nd}$ Ed., 1994); *The Cambridge Dictionary of Science and Technology* (Walker, Ed., 1988); *The Glossary of Genetics*, 5$^{th}$ Ed., Rieger et al., Eds., Springer-Verlag; 1991); and *The Harper Collins Dictionary of Biology* (Hale and Marham, Eds.; 1991).

Additional methods and compositions similar or equivalent to one or more of those described herein may also be employed in the use or in the testing of rAAV vector compositions, methods, and formulations described herein. For purposes of this disclosure, the following terms are defined below for sake of clarity and ease of reference:

In accordance with long standing patent law convention, the words "a" and "an" when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion media, coating(s), diluent(s), buffer(s), isotonic agent(s), solution(s), suspension(s), colloid(s), inert(s), or such like, or a combination thereof that is pharmaceutically acceptable for administration to the relevant animal or acceptable for a therapeutic or diagnostic purpose, as applicable.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "effective amount," as used herein, refers to an amount that is capable of treating or ameliorating a disease or condition or otherwise capable of producing an intended therapeutic effect.

The term "for example," or "e.g.," as used herein, is used merely by way of example, without limitation intended, and should not be construed as referring only those items explicitly enumerated in the specification.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

As used herein, "heterologous" is defined in relation to a predetermined referenced gene or protein sequence. For example, with respect to a structural gene sequence, a heterologous promoter is defined as a promoter which does not naturally occur adjacent to the referenced structural gene, but which is positioned thereto by laboratory manipulation. Likewise, a heterologous gene or nucleic acid segment is defined as a gene or segment that does not naturally occur adjacent to the referenced promoter and/or enhancer elements, but is placed thereby through one or more laboratory techniques.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of reagents, components, or pharmaceutically-formulated rAAV vector-based compositions disclosed herein. Optionally, such kit may include one or more sets of instructions for use of one or more of the disclosed viral-vector-based compositions, such as, for example, in a laboratory or clinical application.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally-occurring animals.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In certain embodiments, the mammalian patient is preferably human.

The phrase "pharmaceutically-acceptable" refers to molecular entities and compositions that preferably do not produce an allergic or similar untoward reaction when administered to a mammal, and in particular, when administered to a human.

As used herein, "pharmaceutically-acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "pharmaceutically-acceptable salt" as used herein refers to a compound of the present disclosure derived from pharmaceutically-acceptable bases, inorganic or organic acids. Examples of suitable acids include, but are not limited to, hydrochloric, hydrobromic, sulfuric, nitric, perchloric, fumaric, maleic, phosphoric, glycolic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys) Amino acid residues described herein are preferred to be in the "L" isomeric form. However, residues in the "D" isomeric form may be substituted for any L-amino acid residue provided the desired properties of the polypeptide be retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins may include those that have been post-translationally modified, and those that include any sugar or other derivative(s) or conjugate(s) added to the backbone amino acid chain.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "recombinant" indicates that the material (e.g., a polynucleotide or a polypeptide) has been artificially or synthetically (non-naturally) altered by human intervention. The alteration can be performed on the material within or removed from, its environment, or natural state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The term "a sequence essentially as set forth in SEQ ID NO:X" means that the sequence substantially corresponds to a portion of SEQ ID NO:X, and has relatively few nucleotides (or amino acids in the case of polypeptide sequences) that are not identical to, or a biologically-functional equivalent of, the nucleotides (or amino acids) of SEQ ID NO:X. The term "biologically-functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions include, for example, hybridization in 50% formamide, 5×Denhardt's solution, 5×SSC, 25 mM sodium phosphate, 0.1% SDS and 100 µg/mL of denatured salmon sperm DNA at 42° C. for 16 hr followed by 1 hr sequential washes with 0.1×SSC, 0.1% SDS solution at 60° C. to remove the desired amount of background signal. Lower stringency hybridization conditions include, for example, hybridization in 35% formamide, 5×Denhardt's solution, 5×SSC, 25 mM sodium phosphate, 0.1% SDS and 100 µg/mL denatured salmon sperm DNA or E. coli DNA at 42° C. for 16 hr followed by sequential washes with 0.8×SSC, 0.1% SDS at 55° C. Those of skill in the art will recognize that conditions can be readily adjusted to obtain the desired level of stringency.

Naturally, the present disclosure also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present disclosure may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including mammals such as primates, to which treatment with the compositions according to the present disclosure can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

As used herein, the terms "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

As used herein, "synthetic" shall mean that the material is not of a human or animal origin.

The term "therapeutically practical time period" means a time period necessary for the active agent to be therapeutically effective. The term "therapeutically effective" refers to reduction in severity and/or frequency of symptoms, elimination of symptoms and/or underlying cause, prevention of the occurrence of symptoms and/or their underlying cause, and improvement or remediation of damage.

A "therapeutic agent" may be any physiologically or pharmacologically active substance that may produce a desired biological effect in a targeted site in a subject.

As used herein, a "transcription factor recognition site" and a "transcription factor binding site" refer to a polynucleotide sequence(s) or sequence motif(s) that are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to those of skill in the art.

"Transcriptional regulatory element" refers to a polynucleotide sequence that activates transcription alone or in combination with one or more other nucleic acid sequences. A transcriptional regulatory element may comprise, for example, one or more promoters, one or more response elements, one or more negative regulatory elements, and/or one or more enhancers.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the terms "treat," "treating," and "treatment" refer to the administration of one or more compounds (either alone or as contained in one or more pharmaceutical compositions) after the onset of clinical symptoms of a disease state so as to reduce, or eliminate any symptom, aspect or characteristic of the disease state. Such treating need not be absolute to be deemed medically useful. As such, the terms "treatment," "treat," "treated," or "treating" may refer to therapy, or to the amelioration or the reduction, in the extent or severity of disease, or to the lessening or diminuation of one or more symptoms thereof, in a patient.

The term "vector," as used herein, refers to a nucleic acid molecule (typically comprised of DNA) capable of replication in a host cell and/or to which another nucleic acid segment can be operatively linked so as to bring about replication of the attached segment. Plasmids, cosmids, viruses, and infectious virions are all examples of vectors in this context.

In certain embodiments, it will be advantageous to employ one or more nucleic acid segments (polynucleotides) of the present disclosure in combination with one or more appropriate detectable marker(s) (i.e., a "label(s)"), such as in the case of employing labeled polynucleotide probes for determining the presence of a given target sequence in a detection assay, such as a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents.

In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

The section headings used throughout are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Exemplary rAAV Vectors

Studies in which primary bovine vascular endothelial cells were infected with several AAV2 based capsid mutants carrying CBA promoter driving green fluorescent promoter (CBA-GFP) resulted in robust GFP expression in the AAV2 (QuadY→F+T→V) treated cells (see, e.g., FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L). Transduction efficiencies were determined 3 days post infection by fluorescence-activated cell sorting (FACS). Transduction efficiency of cells treated with AAV2(QuadY→F+T→V) was over 60% of cells positive at a multiplicity-of-infection (MOI) of $10^4$ particles/cell.

Figure 1B:
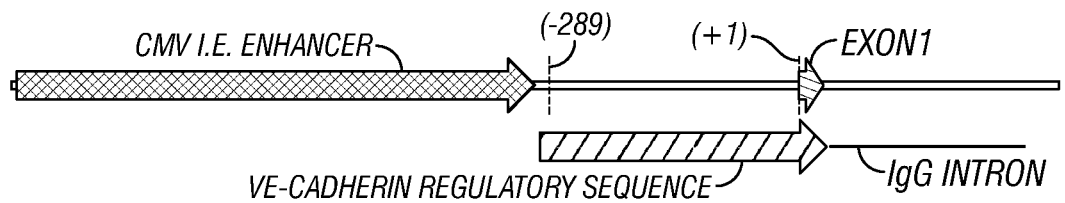
Figure 3F:
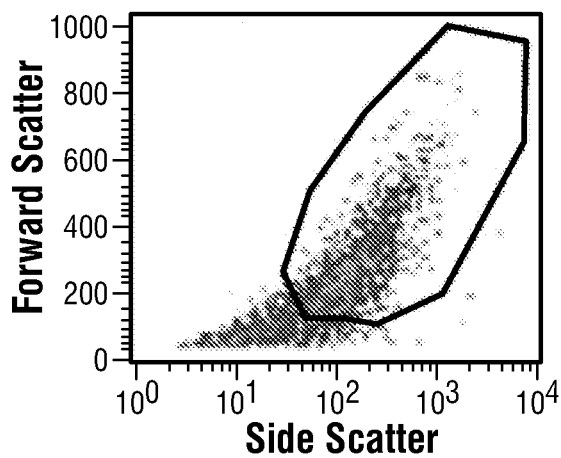
Figure 3G:
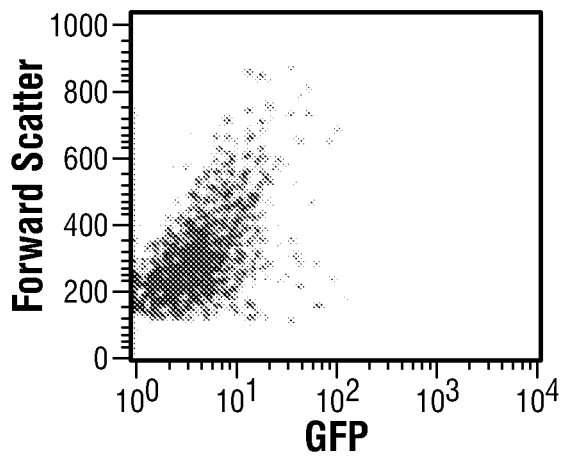
Figure 3H:
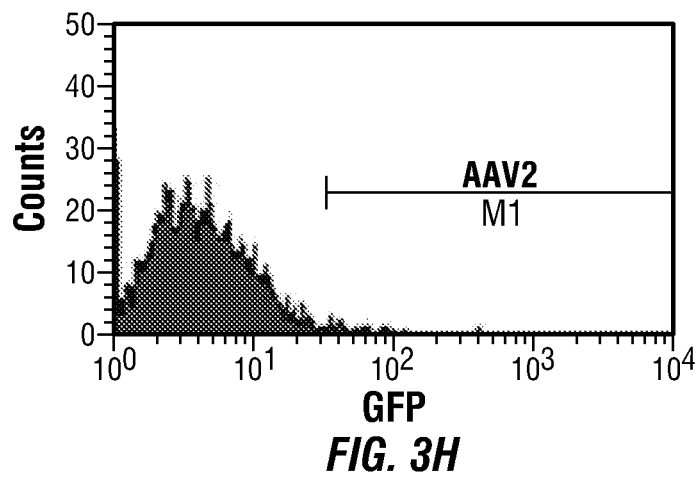
Figure 3I:
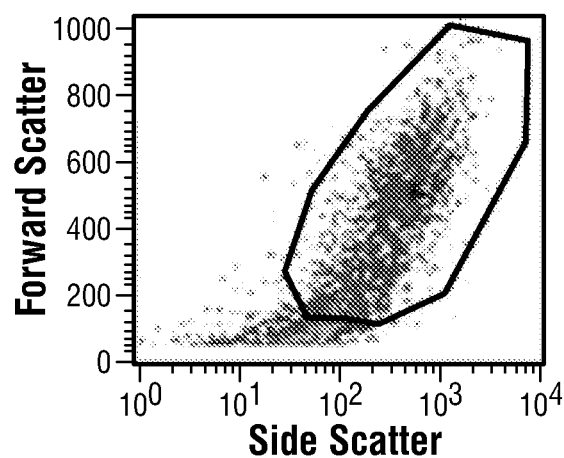
Figure 3J:
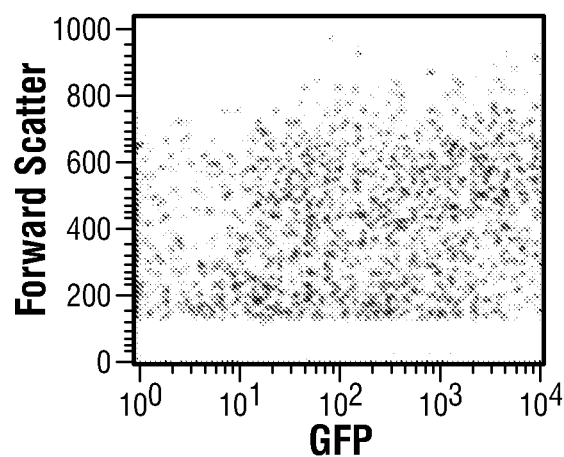
Figure 3K:
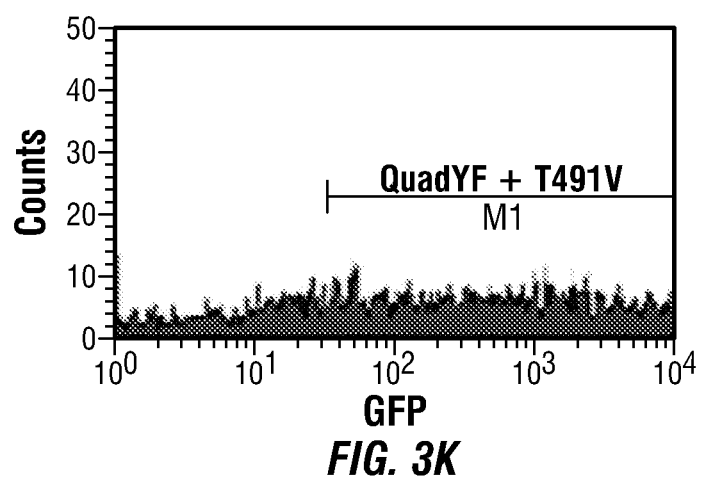
Figure 3L:
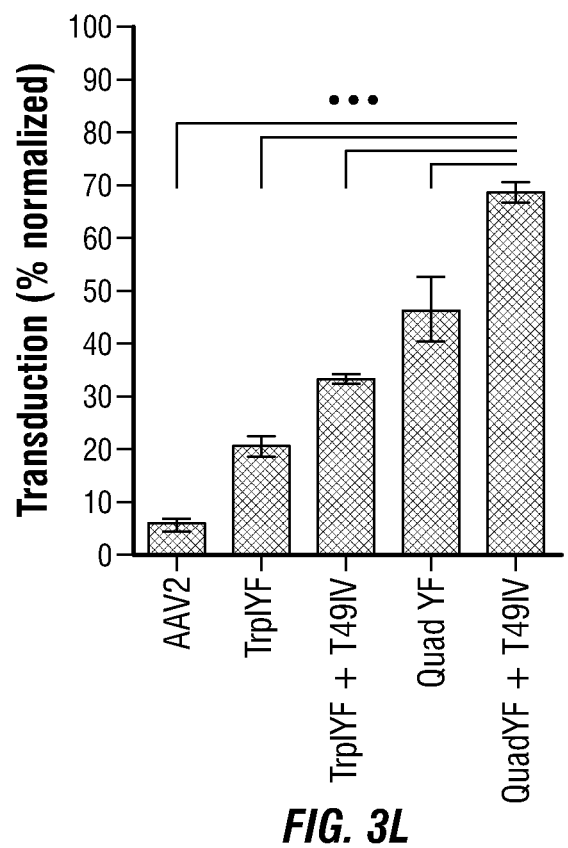
Figure 4A:
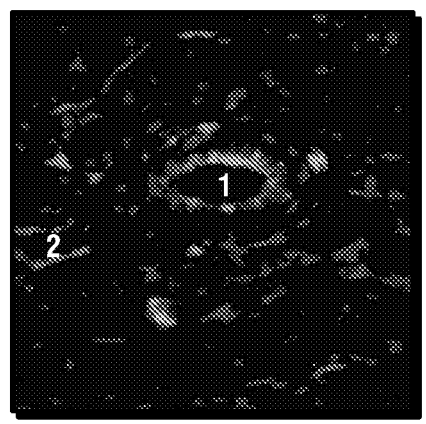
FIG. 4A, FIG. 4B, FIG. 4C, and FIG. 4D show the histological examination of organs harvested from mice injected intravenously with QuadYF+T491V vector expressing GFP from an endothelial cell specific promoter (VECad).
Figure 4B:
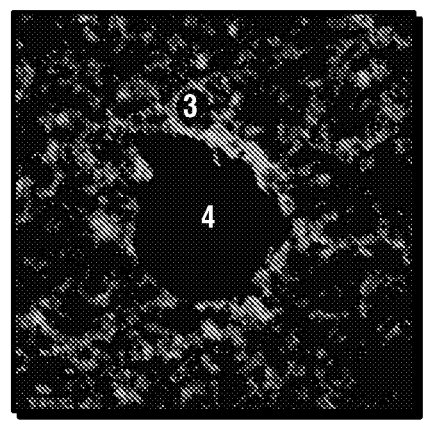
Figure 4C:
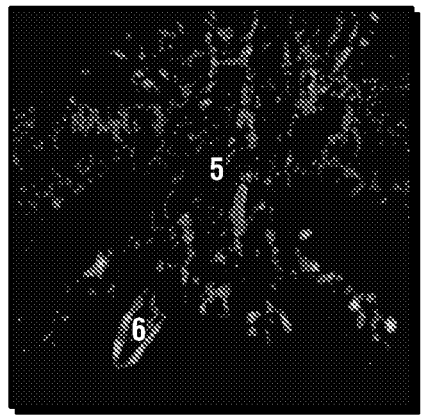
Figure 4D:
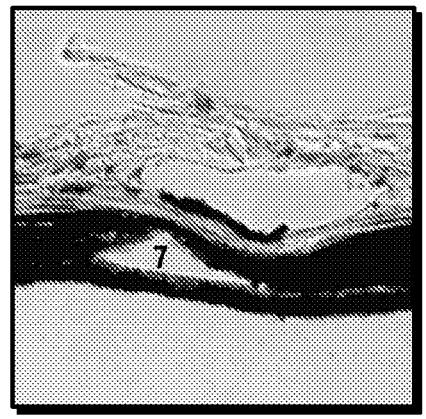

In order to restrict expression of transgene to the vascular endothelium we developed VEC-targeting promoters. Importantly, these promoters are of sufficiently small size to allow for the incorporation of up to ~3,000 nucleotides of DNA within a recombinant AAV vector. These chimeric promoters incorporate specific regulatory regions of the human VE-cadherin gene (−289 to +1 and a portion of exon 1), which have been fused to a chimeric Immunoglobin G Intron as originally used in expression vector pRK5, and in the case of CMV-smVEcad, the immediate early enhancer of Cytomegalovirus. Diagrams depicting the arrangement of elements within each promoter are presented in FIG. 1A and FIG. 1B, respectively.

To test selectivity and efficiency of expression in vivo, wildtype (C57bl6) mice were injected intravascularly with AAV2(QuadY→F+T→V) containing smVECad-GFP or CMV-smVECad-GFP. The mice were sacrificed 4-weeks' post-injection, and retinas were flat-mounted, and then evaluated for raw GFP fluorescence. FIG. 2A, FIG. 2B, and FIG. 2C show transduction of retinal vasculature by AAV2 (QuadY→F+T→V)-smVECad-GFP. Results were comparable for AAV2(QuadY→F+T→V)-CMV-smVECad-GFP.

Example 2

Vascular-Targeting AAV Vectors for Treating Complications of Diabetes and Other Vascular Diseases This Example describes the evaluation of toxicity and therapeutic efficacy of an intravenously-administered adeno-associated virus (AAV)-mediated gene therapy aimed at preventing the development of vascular complications associated with type I diabetes. The study exploits over expression of GTP cyclohydrolase 1 (Gch1), the rate-limiting enzyme that catalyzes the de novo biosynthesis of a cofactor, which acts to stabilize endothelial nitrox oxide synthase (eNOS) (Forstermann and Munzel, 2006).

To successfully transduce VECs, it is necessary to utilize vector constructs that are delivered in capsid-mutated AAV virions. In particular, the present disclosure provides vectors packaged in novel, pentuple-capsid mutant AAV particles, that contain four tyrosine-to-phenylalanine mutations (at amino acid positions Y272F, Y444F, Y500F, and Y730F), and a threonine-to-valine mutation at amino acid position T491V (amino acid positions corresponding to the AAV2 wild-type capsid sequence shown in SEQ ID NO:2). This pentuple mutant is alternatively referred to herein as "AAV2 (QuadYF/TV)" or "AAV2(QuadY→F+T491V)".

First, as vascular endothelial cell dysfunction underlies both the microvascular and macrovascular pathologies associated with diabetes, it is likely that the administration of a gene therapy targeted towards relieving endothelial cell dysfunction may result in amelioration or prevention of pathological changes in organs other than the eye. To test this hypothesis, a detailed histological assessment of >15 target organs harvested from QuadYF-T491V.Gch1 treated STZ-diabetic mice may be performed in comparison to untreated age-matched diabetic controls for signs of pathological changes associated with long-term diabetes, such as thickening of vascular basement membranes.

Second, with treatment necessitating the intravenous administration of large numbers of AAV genome particles (~1×10$^{12}$ gp per animal) there exists the potential for vector-related toxicity. To examine this possibility, a pathological assessment may be conducted of organs harvested from QuadYF+T491V.Gch1 treated non-diabetic mice in comparison to age matched, non-treated, non-diabetic control animals for signs of vector-related toxicity, such as inflammation. In addition to the above histo-pathological assessments, the number of vector genomes present at the tissue level may be quantified in experimental animals, allowing correlations to be drawn between evidence of therapeutic efficacy and/or vector-related toxicity and vector genome distribution.

Third, whilst Type I diabetes is a disease that affects multiple organ systems, the disease's prevalence (1 in 100, in the United States), and the likely requirement for large vector volumes means it would be impractical to administer a systemic gene therapy to an appreciable percentage of those afflicted. With therapeutic efficacy likely correlated directly to the extent of vascular endothelial transduction within a given organ, effective treatment may be best achieved, however, by restricting vector distribution to a small section of the vasculature, or to a particular target organ.

The transduction efficiency and systemic vector genome distribution of AAV(QuadY→F–T→V) vectors expressing either luciferase (Luc) or green fluorescent protein (GFP) may therefore be assayed when a small vector volume is administered into a temporarily occluded section of vasculature. High levels of localized transduction can thus be achieved using a small vector dose, and systemic distribution of vector genomes can therefore be substantially reduced, thus significantly limiting the potential for toxicity and/or an immune response.

A study was undertaken to determine the wider therapeutic efficacy and toxicity of AAV-mediated Gch1 overexpression at ameliorating vascular complications of T1D. The example describes the detailed histopathological assessment of all organs (>15 tissues) harvested from Gch1-treated STZ-diabetic and control mice. Pathological findings of therapeutic efficacy, such as reduced basement membrane thickening, or toxicity, such as inflammation and cell death, was correlated with AAV vector distribution as quantified by the presence of vector genomes within each tissue.

In addition to evaluating the therapeutic effect and potential for toxicity following systemic administration, optimized delivery of vectors such as AAV(QuadY→F+T491V) may facilitate the translation of AAV-mediated Gch1 gene therapy into clinically-relevant treatment modalities. Specifically, transduction efficiency and systemic distribution of the AAV(QuadY→F+T491V) vector can be assessed when delivered to a temporarily-occluded section of the vasculature. By restricting vector administration to a small section of the vasculature it was hypothesized that:

1) the vector volume required per patient organ could be significant reduced;

2) transduction efficiency could be increased through maximizing virion contact time with the vascular endothelium;

3) ectopic expression and potential toxicity could be limited by reducing systemic distribution; and 4) immune recognition by circulating neutralizing antibodies and sequestration by lymphoid tissues (e.g., the spleen) (Mori et al., 2006) could be limited.

The later is of particular relevance where, unlike naïve experimental animals, up to 30% of humans have neutralizing antibodies towards AAV2 (Moskalenko et al., 2000; Halbert et al., 2006), and even low antibody titers can have a profound negative effect on transduction efficiency (Hurlbut et al., 2010; Manno et al., 2006; Tseng and Agbandje-McKenna, 2014).

In order to model the effects of restricted vascular delivery on transduction efficiency and systemic distribution temporary occlusion of the tail vein may be achieved by application of a tourniquet at the tail's base prior to intravenous injection of a small vector dose. In humans, this principle could be extended to isolate vector delivery to individual organs, or sections of vasculature, through direct cannulation.

For the treatment of DR, this can be achieved through a process similar to that employed for intraarterial (ophthalmic artery) chemotherapy (Abramson et al., 2008; Peterson et al., 2011), and may be combined with temporary occlusion of the ophthalmic vein to prevent virion egress from the retinal and/or choroidal vasculature. In humans, permissible occlusion duration is likely to be organ dependent; however, in cases of central retinal artery occlusion, irreversible ischemic injury does not occur for 1-2 hrs (Hayreh et al., 2004), indicating that a wide potential treatment window may exist.

Compared to other Y-to-F mutant AAV vectors that have been described in the literature (Petrs-Silva et al., 2011; Petrs-Silva et al., 2009; Thong et al., 2008a; Zhong et al., 2008b), the pentuple capsid-mutated AAV(QuadY→F+T→V) vectors described herein permit effective targeting of vascular endothelium via intravenous administration. To date, no other AAV vector has been shown to possess such high efficiency delivery of a transgene to vascular endothelial cells.

The treatment of vascular endothelial cell dysfunction is vital for preventing diabetic vascular complications, and yet the therapeutic approach developed herein may also be applied for other diseases affecting the vasculature, including hypercholesterolemia and hypertension. By modeling restriction of vector delivery, substantial improvement exists for the likelihood of vectors such as the AAV(QuadY→F+T→V) vectors described herein being applicable clinically, and any vascular complications that may arise, can be addressed by treatment of affected organs separately, allowing lower vector doses, whilst simultaneously increasing treatment efficacy and specificity.

It was reported that epidermal growth factor receptor protein tyrosine kinase (EGFK-PTK)-mediated tyrosine phosphorylation of exposed surface residues of the AAV capsid promotes ubiquitination and subsequent proteasomal degradation of AAV particles, and that this process decreases AAV vector transduction efficiency (Zhong et al., 2008a; Thong et al., 2008b).

Site-directed tyrosine-to-phenylanine (Y→F) mutagenesis of selected tyrosine residues in AAV2 was shown to protect vector particles from proteasomal degradation and significantly increase the transduction efficiency of these mutant AAV vectors relative to the wild-type AAV vectors. Further improvements to transduction efficiency may also be achieved through site-directed threonine-to-valine (T→V) mutagenesis, which further aid to decrease phosphorylation of the capsid, preventing ubiquitination (Gabriel et al., 2013; Kay et al., 2013).

It has been shown that vectors with capsid mutations display a strong and widespread transgene expression in many retinal cell types following intraocular delivery (Petrs-Silva et al., 2011; Petrs-Silva et al., 2009; Zhong et al., 2008a; Thong et al., 2008b).

To assess whether various Y→F and T→V multi-capsid-mutated vectors could be utilized to effectively deliver transgenes to endothelial cells, the ability of four vectors with multiple capsid mutations packaging a GFP reporter marker to transduce primary bovine retinal vascular endothelial cells in vitro was examined. Those results are shown in Table 1:

TABLE 1

NOMENCLATURE OF EXEMPLARY AAV2-DERIVED MUTATED CAPSID VECTORS

| Vector | Mutated Amino Acid Residues in Capsid |
|---|---|
| AAV2 (wild-type) | None |
| TrplYF | Y444F, Y500F, Y730F |
| TrplYF + T491V | Y444F, Y500F, Y730F, T491V |
| QuadYF | Y272F, Y444F, Y500F, Y730F |
| QuadYF + T491V | Y272F, Y444F, Y500F, Y730F, T491V |

Compared to the unmodified, wild-type AAV2, all capsid mutant vectors demonstrated substantially higher levels of GFP expression (see FIG. 3A, FIG. 3B, FIG. 3C, FIG. 3D, and FIG. 3E). Expression levels were observed to increase with the number of capsid residues mutated. The QuadYF+T491V vector clearly demonstrated the highest transduction level (FIG. 3E), indicating an additive effect of the capsid modifications. Quantification of GFP-positive cells (n=3 wells per vector) by flow cytometry confirmed that significantly more vascular endothelial cells were transduced using the QuadYF+T491V vector than other multiple-mutant vectors or unmodified AAV2 (FIG. 3F, FIG. 3G, FIG. 3H, FIG. 3I, FIG. 3J, FIG. 3K, and FIG. 3L).

In view of the efficiency of the QuadYF+T491V vector at transducing retinal endothelial cells in vitro, the in vivo transduction efficiency of murine endothelial cells was examined following intravenous delivery of QuadYF+T491V vector packaging a GFP-reporter gene under control of a vascular endothelial cell cadherin (VECad) promoter (QuadYF+T491V.GFP). Each animal received a high dose ($\sim 1\times10^{12}$ gp per mouse) intravenous injection of QuadYF+T491V.GFP suspended in 200 µL balanced salt solution (BSS) via injection into the retro-orbital venous sinus (peri-orbital injection). Four weeks post-injection, the mice were fixed by transcardial perfusion of 4% paraformaldehyde (PFA) and the organs harvested for histology. The kidneys (A), liver (B), eyes (C-D) and lungs of all animals injected demonstrated GFP fluorescence that was predominantly restricted to the walls of major blood vessels. The tissue surrounding transduced blood vessels was frequently observed to be fluorescent, indicating that the endothelial cell specific promoter has some ectopic activity. However, transgene expression with the VECad promoter was substantially more restricted compared to intravascular delivery of a ubiquitously expressing reporter construct (CBA.GFP), particularly in the liver where widespread hepatocyte transduction was observed. These data demonstrated that a transgene could be successfully delivered to VECs using a QuadYF+T491V capsid mutant vector, and provided evidence for the use of the QuadYF+T491V capsid mutant AAV vector to deliver therapeutic transgenes, including Gch1, to reduce endothelial cell dysfunction, including that present in mammalian Type I diabetes.

Figure 5A:
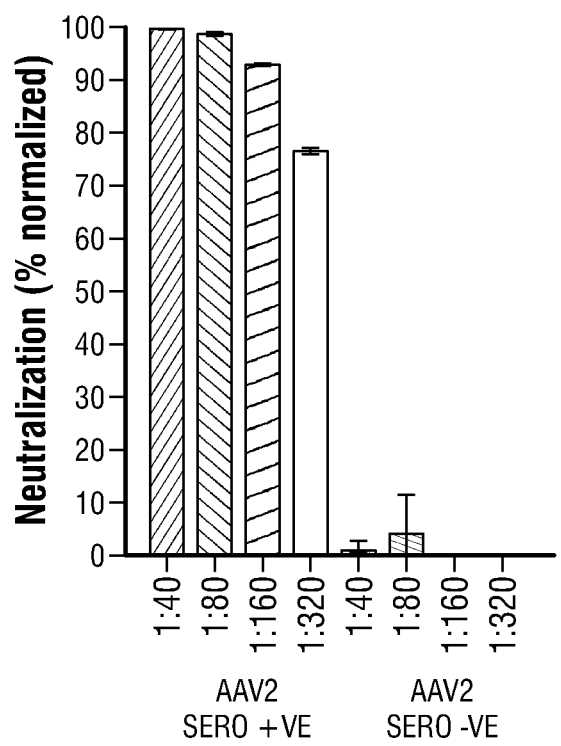
FIG. 5A and FIG. 5B show results of an antibody neutralization assay demonstrating cross-reactivity of AAV2 positive primate serum at two-fold dilutions (1:40-1:320).
Figure 5B:
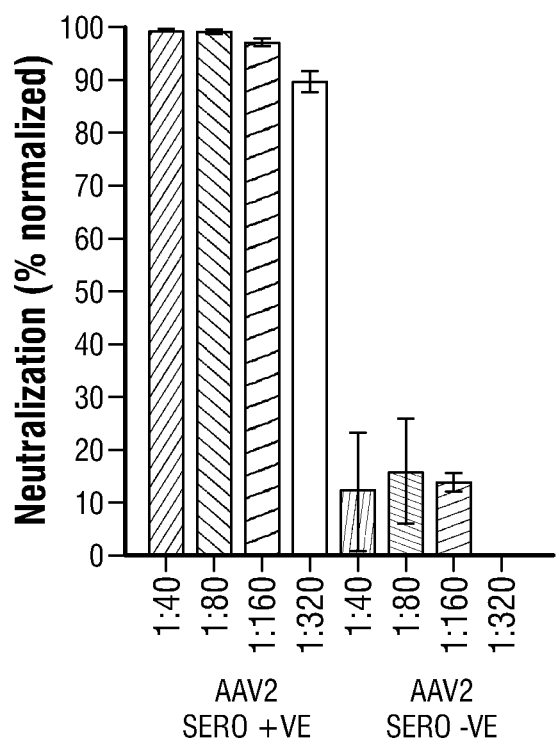

Numerous studies have demonstrated that the exposure of an experimental animal to virus vector stimulates robust production of serotype-specific neutralizing antibodies. These neutralizing antibodies effectively prohibit re-administration of the same vector serotype as they efficiently sequester and inactivate virions (Xiao et al., 1999; Fisher et al., 1997; Halbert et al., 1997; Manning et al., 1998). As neutralizing antibodies are typically raised against specific conserved regions of the capsid, the cross-reactivity of antibodies raised against unmodified AAV2 was evaluated to neutralize infectivity of the QuadYF+T491V capsid mutant vector. Using serum obtained from primates with high (sero+ve) or low (sero−ve) levels of neutralizing antibodies towards unmodified AAV2, QuadYF+T491V and AAV2 vectors packaging a self-complimentary mCherry reporter construct were pre-incubated, and their ability to transduce ARPE19 cells was assessed by flow cytometry. As expected, AAV2 seropositive (+ve) serum effectively neutralized unmodified AAV2 vector at low serum dilution (FIG. 5A). QuadYF+T491V vector was also efficiently neutralized by AAV2-positive serum, demonstrating that the capsid mutations did not confer any beneficial immune evasion properties. Indeed, it was noted that the QuadYF+T491V vector was neutralized to a somewhat, but not significantly greater extent than unmodified AAV2. This observation was confirmed when QuadYF+T491V was pre-incubated with serum containing low levels of anti-AAV2 antibodies, leading to neutralization exceeding that of unmodified AAV2 exposed to the same serum. Whilst sequestration of QuadYF+T491V virions by neutralizing antibodies is not a concern when treating endothelial cell dysfunction, where all experimental animals are naïve to AAV exposure, circulating antibodies could have significant implications for systemic treatment of type I diabetes in humans, most of whom have pre-existing immunity to AAV (Moskalenko et al., 2000; Halbert et al., 2006).

Materials and Methods

The overall experimental strategy utilized the highly-efficient QuadY→F+T→V pentuple-mutant capsid AAV2-based vector described above to transduce vascular endothelial cells and overexpress the Gch1 transgene. The study assessed all organs harvested from experimental animals for signs of therapeutic efficacy as a result of reduced endothelial cell dysfunction, and for toxicity related to systemic vector administration. To increase translatability of the resulting gene therapy, delivery of a small vector volume into a temporarily occluded section of the vasculature is examined to determine whether such manipulation might result in robust endothelial cell transduction yet with a greatly reduced vector dose.

Examination of the therapeutic efficacy of QuadYF+T491V.Gch1 at ameliorating endothelial cell dysfunction in Tg(Cspg4.DsRed$^{+/-}$ Tie2.EGFP$^{+/-}$) STZ-diabetic mice. Organs are harvested from QuadYF+T491V.Gch1-injected ($1\times10^{12}$ gp per mouse) Tg(Cspg4.DsRed$^{+/-}$ Tie2.EGFP$^{+/-}$) STZ-diabetic mice and age-matched, untreated Tg(Cspg4.DsRed$^{+/-}$ Tie2.EGFP$^{+/-}$) STZ-diabetic control mice and examined for signs of therapeutic efficacy at 3, 6, 9 and 12 months post-induction of STZ diabetes. Each group contains 10 mice that originated from at least three separate litters. 15 tissues (heart, spleen, kidney(s), brain, pancreas, lung(s), cerebellum, eye(s), medulla oblongata, spinal cord, mesenteric lymph nodes, liver, distal esophagus, blood, peripheral muscle) and any observed gross lesion(s) are harvested at necropsy in a manner that avoids cross-contamination according to established GLP-compliant biodistribution protocols. Trimmed tissue for pathological assessment are fixed by immersion in 4% PFA (i.e., 10% formalin) overnight at room temperature (RT); trimmed tissue for quantification of genome particles are snap frozen in liquid nitrogen, and then stored at −80° C. until genomic DNA is extracted as previously described (Poirier et al., 2004; Song et al., 2002).

A detailed histopathological assessment is performed on tissue samples harvested from QuadYF+T491V.Gch1-injected Tg(Cspg4.DsRed$^{+/-}$ Tie2.EGFP$^{+/-}$) STZ-diabetic mice and age-matched, untreated Tg(Cspg4.DsRed$^{+/-}$ Tie2.EGFP$^{+/-}$) STZ-diabetic control mice to determine the degree of therapeutic efficacy. Tissues that were fixed in 4% PFA are trimmed and embedded in both paraffin and optimal cutting temperature (OCT) medium. Paraffin-embedded sections are sectioned at 5 µm, and stained with hematoxylin and eosin (H&E); additionally kidney samples are stained with a periodic acid Schiff (PAS). The resulting tissue sections are examined and all pathological findings are entered directly into a validated pathology computer program (Provantis® NT 2000, Data Management System with fully described topographical "locators" and "modifiers." Modifiers included severity grades of minimal, mild, moderate, and marked, where appropriate. These assays are performed adherent to GLP regulations and adhere to internal SOPs. OCT-embedded sections are sectioned at 5 µm, and are used for direct fluorescence microscopy, and immunohistochemical staining for Gch1 expression. Assessment of harvested eyes is performed as previously described; briefly, retinal thickness in all animals is assessed by optical coherence tomography (OCT), a non-invasive imaging technique that allows retinal thickness to be measured through the pupil under anesthesia. Quantification of retinal pericyte numbers and formation of acelluar capillaries is performed post-mortem on retinas following trypsin digestion to expose the vasculature. The second eye from each animal is utilized for quantification of vector genomes.

Quantification of vector genomes is performed on tissue samples harvested from QuadYF+T491V.Gch1 injected Tg(Cspg4.DsRed$^{+/-}$ Tie2.EGFP$^{+/-}$) STZ-diabetic mice and age-matched untreated Tg(Cspg4.DsRed$^{+/-}$ Tie2.EGFP$^{+/-}$) STZ-diabetic control mice. Genomic DNA (gDNA) was isolated from all tissues (n=15 per animal) according to established GLP-compliant biodistribution protocols, and the concentration determined by spectrophotometry. The number of rAAV genome copies present in each tissue was assessed by qPCR using primers and probes designed to the SV40 poly-a of the Gch1 vector cassette. DNA samples were assessed in triplicate; in order to assess PCR inhibition, the third replicate was routinely spiked with plasmid DNA at a ratio of 100 copies/µg gDNA with the results normalized as per internal SOPs. The number of vector genomes present in each tissue was closely correlated with histo-pathological evidence of therapeutic efficacy.

Examination of tissues for any toxicity resulting from intravenous administration of QuadYF+T491V.Gch1 vector in Tg(Cspg4.DsRed$^{+/-}$ Tie2.EGFP$^{+/-}$) non-diabetic mice. Breeding of Tg(Cspg4.DsRed$^{+/-}$ Tie2.EGFP$^{+/-}$) is performed to produce animals for assignment to the non-diabetic, QuadYF+T491V.Gch1 treated study arm. Mice are bred by crossing the Tg(Cspg4-DsRed.T1$^{+/-}$) and Tg(Tie2-GFP$^{+/+}$) mouse strains, which are currently breeding well and maintained in the laboratory. Due to the Heterozygote× Homozygote breeding strategy employed, it is anticipated that breeding of 80 mice is required to obtain 40 animals of the correct genotype; animals of incorrect genotype will be culled. Crossbreeding of these strains is usually productive (non-lethal, 5-8 pups per litter) and four breeding pairs are typically sufficient for this purpose. Mice are assigned randomly to the three-, six-, nine- or 12-month treatment groups, with each group comprising 10 mice from at least three separate litters. All experimental animals receive an intravenous dose of $1\times10^{12}$ gp (200 µL total volume in BSS) QuadYF+T491V.Gch1 vector via retro-orbital injection at post-natal week 8. Once experimental time points are reached, mice were euthanized and processed.

Organs were harvested from QuadYF+T491V.Gch1 injected ($1\times10^{12}$ gp per mouse) Tg(Cspg4.DsRed$^{+/-}$ Tie2.EGFP$^{+/-}$) non-diabetic mice and age matched untreated Tg(Cspg4.DsRed$^{+/-}$ Tie2.EGFP$^{+/-}$) non-diabetic control mice for signs of toxicity at three-, six-, nine-, and 12-months post-induction of STZ diabetes. Each group contains 10 mice that originate from at least three separate litters. Organs were harvested and processed as described above.

A detailed histopathological assessment was performed on tissue samples harvested from QuadYF+T491V.Gch1-injected Tg(Cspg4.DsRed$^{+/-}$ Tie2.EGFP$^{+/-}$) non-diabetic mice and age-matched, untreated Tg(Cspg4.DsRed$^{+/-}$ Tie2.EGFP$^{+/-}$), non-diabetic control mice to assess evidence of vector related toxicity. Histology and subsequent assessments are performed as described above.

Quantification of vector genomes is performed on tissue samples harvested from QuadYF+T491V.Gch1-injected, Tg(Cspg4.DsRed$^{+/-}$ Tie2.EGFP$^{+/-}$), non-diabetic mice and age-matched, untreated Tg(Cspg4.DsRed$^{+/-}$ Tie2.EGFP$^{+/-}$), non-diabetic control mice. Quantification of vector genomes was performed as described above, and the number of vector genomes present in each tissue was closely correlated with histopathological evidence of toxicity, as assessed above.

Optimization of intravenous QuadYF+T491V vector administration to increase transduction efficiency and limit systemic distribution in Balb/cj mice. A study may be performed to assess the efficiency with which QuadYF+T491V.GFP vector transduces vascular endothelial cells when administration is restricted to a temporarily occluded section of vasculature. Adult Balb/cj mice (60 in total) may be used for such an experiment, due to the absence of pigmentation. As a model of temporary vascular occlusion, blood flow may be restricted to the tail under anesthesia by application of an umbilical tape tourniquet at the tail's base, followed immediately by injection of low dose (up to $1\times10^{11}$ gp; 20 µL total volume in BSS) QuadYF+T491V.GFP vector directly into a lateral tail vein. The period that the QuadYF+T491V.GFP vector is allowed to remain in the tail vein before normal blood supply is restored can range from one to 10 min in one-min increments (10 groups, n=3 mice per group). Once normal blood flow is restored, mice are returned to their home cages and monitored for signs of traumatic injury associated with application of the tourniquet. Control animals (10 groups, n=3 mice per group) consist of mice receiving an equivalent dose of QuadYF+T491V.GFP vector and kept under anesthesia (i.e., immobilized) for the same duration. Transgene expression is permitted for four weeks, at which point the mice are euthanized and the tails harvested for histology. Cross-sections of the tail are taken at 1-cm intervals from the point of tourniquet application to the tail tip and assessed for evidence of GFP expression the injected vein and connecting vasculature (e.g., dorsal artery). A pathological assessment may be made to assess evidence of ischemic or reperfusion injury caused by the temporary occlusion.

An assessment may be made of systemic transduction and genome distribution following administration of QuadYF+T491V.Luc vector into an occluded section of the tail vasculature and compared to vector distribution when the vein is not occluded. The study may consist of two experimental groups (n=5 mice per group) each receiving intravascular delivery of low dose (up to $1\times10^{11}$ gp; 20 µL total volume in BSS) QuadYF+T491V.Luc vector into an occluded or un-occluded tail vein; the length of time that the tail vein remains occluded is determined as described above. Four-weeks' post-injection, animals may undergo whole-body imaging to assess the extent of systemic vector administration, because of leakage past the vessel occlusion and circulation of unbound vector particles once normal blood flow has been restored. Briefly, animals are anesthetized by isofluorane and injected intraperitoneally with luciferin solution (D-luciferin; 150 mg/kg) immediately prior to whole-body imaging. Imaging detects bioluminescence associated with transgenic expression of firefly luciferase, which acts to catalyze the oxidation of D-luciferin substrate to oxyluciferin in the presence of ATP, $Mg^{2+}$ and oxygen. Following imaging, organs from each experimental animal may be harvested and processed for analysis of genome particle distribution. Assessment of genome particle distribution allows for a comparison of whether vector administration into a temporarily occluded section reduces systemic genome distribution that may lead to ectopic expression and/or vector-related toxicity.

Animal Model. In this example, the therapeutic effect of Gch1 over-expression on endothelial cell dysfunction was studied in an STZ-diabetic double-fluorescent reporter mouse. This reporter mouse expressing discosoma red fluorescent protein (DsRed) in pericytes and GFP in vascular endothelial cells was created by crossing of Tg(Cspg4-DsRed.T1) and Tg(Tie2-GFP) mouse strains. Due to their intrinsic fluorescence the resulting Tg(Cspg4.DsRed$^{+/-}$ Tie2.EGFP$^{+/-}$) mice are ideally suited for quantification of pericyte loss and assessment of vascular pathology, and are currently breeding well and maintained in the laboratory. Diabetes in the Tg(Cspg4.DsRed$^{+/-}$ Tie2.EGFP$^{+/-}$) mouse is induced at post-natal week (PW) 12 by two low-dose (100 mg/kg) IP injections of STZ. QuadYF+T491V.Gch1 treatment is administered fours week prior to induction of diabetes (PW8) in treatment groups. Organs from all animals are harvested three, six, nine, and 12 months following STZ induction (or sham citrate buffer administration in control animals).

Organs harvested after QuadYF+T491V.Gch1 treatment are used to assess therapeutic efficacy and toxicity when the vector is administered systemically at high dose. The systemic effects of QuadYF+T491V.Gch1 therapy may be assessed without the need for an independent study. At selected times after treatment, animals are anesthetized and then sacrificed humanely, as described below. Organs are harvested for histopathological, molecular and biochemical analysis. The maximum number of experimental assessments was planned for each tissue harvested to maximize the experimental output of each animal. All procedures described in this example are based upon current IACUC protocols specifically for performing diabetes-related gene therapy analyses.

There are no alternatives to using mice for studying vascular dysfunction resulting from chronic Type I diabetes. Inducement of diabetes in Tg(Cspg4.DsRed$^{+/-}$ Tie2.EGFP$^{+/-}$) mice by administration of STZ allows for straightforward and reproducible quantification of diabetic vascular pathologies, such as acellular capillary formation, basement membrane thickening, and pericyte loss. Induction of diabetes in mice through IP administration of STZ is a well established protocol and results in a reproducible model of type I diabetes that develops many hallmarks of chronic diabetes; no way to replace the use of live animals in order to study the effects of long-term diabetes have been described.

The number of animals planned for the treatment is the minimum required to obtain statistically significant therapeutic endpoints (typically six per treatment cohort) taking into account likely mortality in STZ-diabetic mice over a period of 12 months.

Mice are housed and treated at an ALAAR/USDA-approved facility under SPF conditions. Injectable anesthetic procedure: ketamine (60 mg/kg)/xylazine (10 mg/kg) IP; anesthetic is reversed using 5 mg/kg Antiseden® (atipamezole). Non-injectable anesthesia procedure: Isofluorane, 3-5% (vol./vol.) for induction, 1-4% (vol./vol.) for maintenance (both in oxygen). Topical anesthetic (given in addition to above): one drop of proparacaine hydrochloride (0.5%) to the eye receiving peri-orbital injection. After vector injection, an antibiotic (neomycin/polymyxin B/dexamethasone ophthalmic ointments; Bausch & Lomb, Inc., Temple, Fla., USA) is applied daily to the eye for three days. All animals are monitored daily for signs of adverse effects.

Mice are euthanized by exposure to increasing concentration of carbon dioxide ($CO_2$), followed by confirmation of death by cervical dislocation. Where histology only is required, mice are terminally anesthetized by i.p. injection of xylazine/ketamine to induce a deep surgical plane under which the animal is expected to feel no pain or discomfort prior to euthanasia by transcardial perfusion of 10 mL PBS (exsanguination) followed by fixation (10 mL 4% PFA). Death is confirmed by cervical dislocation prior to organ harvesting.

Example 3

Vectors for Preventing Vascular Complications of Diabetic Retinopathy

This example validates use of the disclosed vascular targeting vectors in mediating the reversal of endothelial nitric oxide synthase (eNOS) uncoupling, and for significantly ameliorating vascular-endothelial dysfunction that is associated with diabetic retinopathy (DR) in Type I diabetic mellitus (T1D). Stabilization of eNOS was achieved by over-expression of GTP cyclohydrolase (GCH1), the rate-limiting enzyme in the de novo synthesis of tetrahydrobiopterin ($BH_4$), an essential co-factor of eNOS, which is depleted in DR. Cell-specific delivery of a therapeutic transgene (murine Gch1) was accomplished using novel capsid-mutant rAAV vectors containing a VEC-specific promoter for efficiently and specifically targeting VECs following intravenous administration.

A double-transgenic reporter mouse with intrinsically fluorescent retinal pericytes (Cspg4-DsRed$^{+/-}$) and vasculature endothelial cells (Tie2-GFP$^{+/-}$) was used to assess the progression of DR over time following ablation of pancreatic β-cells with streptozotocin (STZ). Assessment of the suitability of $BH_4$ stabilization of eNOS as a therapeutic target for preventing vision loss in diabetic retinopathy was made with reference to three primary outcome measures: quantification of retinal pericyte loss, acellular capillary formation, and retinal thinning.

T1D is a chronic metabolic disorder associated with hyperglycemia and characterized by vascular complications including retinopathy, nephropathy, atherosclerotic plaque formation, reduced myocardial perfusion, and inhibition of wound healing (Costa and Soares, 2013). DR is evident in nearly all T1D patients within the first two decades of life, typically presenting as mild non-proliferative diabetic retinopathy (NPDR) which progresses to moderate or severe NPDR characterized by increased vascular permeability, vessel occlusion and diabetic macular edema (Fong et al., 2004). In approximately 30% of cases the disease progresses to proliferative diabetic retinopathy, characterized by blood vessel growth across the surface of the retina and posterior of the vitreous (Fong et al., 2004; Bandello et al., 2013; Ding and Wong, 2012). Underlying both the micro- and macro-vascular complications of T1D is dysfunction of the vascular endothelium associated with increased superoxide production, impaired nitric oxide (NO) synthesis, increased endothelial apoptosis, and decreased endothelium-dependent vasodilation. NO is particularly important in protecting against endothelial dysfunction because it mediates vasodilation through interaction with smooth muscle cells, inhibits platelet aggregation in the vessel lumen, and reduces inflammation by inhibition of leukocyte binding (Forstermann and Munzel, 2006). NO synthesis by eNOS is impaired in DR by reaction of superoxide ($O_2^-$) with vascular NO to form peroxynitrite ($ONOO^-$), an ion that sequesters the stabilizing $BH_4$ co-factor of eNOS. Critically, diminished levels of $BH_4$ lead to eNOS uncoupling, where eNOS produces superoxide rather than NO, and so becomes a contributor to oxidative stress rather than an enzyme that protects against it, thus accelerating vascular dysfunction (Forstermann and Munzel, 2006). It has previously been demonstrated that supplementation of $BH_4$ transiently restores endothelial cell function in vitro (Meininger et al., 2004), in animal models of diabetes (Pieper, 1997) and insulin resistance (Shinozaki et al., 2000), as well in patients with hypercholesterolemia (Stroes et al., 1997), diabetes (Heitzer et al., 2000) and hypertension (Higashi et al., 2002). Although a promising candidate, it has not been possible to validate whether systemic constitutive production of $BH_4$ in vascular endothelial cells is an effective therapeutic strategy for long-term amelioration of endothelial cell dysfunction. This has primarily been due to the difficulty of delivering potentially therapeutic transgenes, such as Gch1, effectively to vascular endothelial cells. However, recent developments focused on AAV vector technology involving mutation of the virus capsid have resulted in vectors that can efficiently target vascular endothelial cells following intravenous injection (see preliminary studies). Whilst intensive glycemic control significantly reduces the mean risk of developing severe microvascular complications in T1D, glycemic regulation is problematic to maintain long-term, usually requiring multiple daily insulin injections. Consequently, reduction of endothelial cell dysfunction by vascular gene therapy, which has the potential to provide life-long protection against the development of vascular complications, such as DR or nephropathy, following a single intervention, presents a promising therapeutic avenue for treatment of T1D. Furthermore, gene therapy to prevent endothelial cell dysfunction has implications for the treatment of macrovascular complications of T1D, such as cardiac disease, which is not improved by glycemic control, and results in significant mortality.

Materials and Methods

Figure 7:
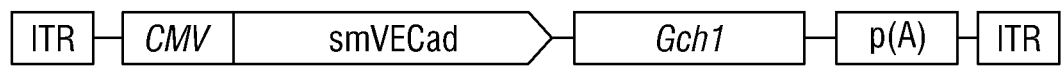
FIG. 7 shows a generalized therapeutic expression cassette in accordance with one aspect of the invention. The forward cistron consists of a vascular endothelial specific promoter (smVECad) driving expression of the tetracycline repressor protein (TetR) and a polyadenylation signal [p(A)] derived from the bovine growth hormone gene. The reverse cistron contains the tetracycline responsive element (TRE) driving expression of Gch1 and a SV40 p(A) signal. When tetracycline or doxycycline is present they sequester the TetR protein preventing it from binding and activating the TRE, consequently preventing expression of Gch1. The cistrons are flanked by AAV inverted terminal repeats (ITR) which allow packaging of the expression cassette into the previously identified mutated capsid (5M).

Vectors. An exemplary bicistronic vector cassette (FIG. 7) was designed to allow inducible expression of a mammalian Gch1 transgene specifically in vascular endothelial cells. The forward cistron consists of a vascular endothelial specific promoter (smVECad) driving expression of the tetracycline repressor protein (TetR) and a polyadenylation signal (p(A)) derived from the bovine growth hormone gene. The reverse cistron contains the tetracycline responsive element (TRE) driving expression of Gch1 and a SV40 p(A) signal. When tetracycline or doxycycline is present they sequester the TetR protein preventing it from binding and activating the TRE, consequently preventing expression of Gch1. The cistrons are flanked by AAV inverted terminal repeats (ITR) which allow packaging of the expression cassette into the previously identified mutated capsid (5M). The virus vector (termed herein as 5M.smVECad-TEToff-Gch1) is routinely purified by iodixanol gradient and fast protein liquid chromatography, resuspended in phosphate buffered saline (PBS) and titered by qPCR using plasmid and virus of known concentration as standards.

Animal Model. A double-fluorescent reporter transgenic mouse, which expresses discosoma red fluorescent protein (DsRed) in pericytes, and green fluorescent protein (GFP) in VECs, was created by crossing of the Tg(Cspg4-DsRed.T1) and Tg(Tie2-GFP) mouse strains (Jax). Tg(Tie2-GFP) mice are homozygous and Tg(Cspg4-DsRed.T1) are heterozygous for the respective transgenic insertion, so crossing resulted in half of all F1 progeny being heterozygous at both loci. At weaning, Tg(Cspg4-DsRed$^{+/-}$ Tie2-GFP$^{+/-}$) mice were identified by genotyping using standard PCR and randomly assigned to either the treatment or control groups. Each control and treatment group initially consisted of 10 mice. Blood glucose levels (BGL) and weight were closely monitored during the experimental time course following induction of diabetes and insulin supplementation provided as appropriate. Mice were group housed in standard 12:12 lighting conditions throughout the experimental time course (see below) with food and water available ad libitum.

Treatment and Induction of Diabetes. At post-natal week (PW) 8, all mice assigned to the treatment groups received an intravenous injection of 32 μL 5M.smVECad-TEToff-Gch1 vector; mice in the control groups received an equivalent volume of PBS. A period of 4 weeks is typically allowed for vector incorporation into vascular endothelial cells during which time expression of the therapeutic transgene is suppressed by doxycycline administration via the drinking water. The control group also receives doxycycline during this period. T1D is induced at PW12 by streptozotocin ablation of pancreatic β-cells. Three days are then allowed for onset of diabetes before BGL was measured (glucose meter); mice with BGL of <250 mg/dL were considered non-diabetic, and were subsequently euthanized. Doxycycline administration is then ceased in the remaining diabetic animals to permit Gch1 transgene expression in vascular endothelial cells.

Experimental Time Course and Analysis. Four experimental cohorts each consisting of a treatment group and paired control group were established as above for analysis at three, six, nine, and 12 months' post-injection. Analysis of DR progression is typically carried out on fixed post mortem tissue, as longitudinal analysis (e.g., fundoscopy, optical coherence tomography) is not possible due to diabetic cataract formation. Analysis focused on the quantification of three primary outcome measures: retinal pericyte loss, acellular capillary formation and retinal thinning using previously published protocols (Li et al., 2010; Verma et al., 2012). Animals were euthanized by perfusion fixation for optimal vascular preservation and the eyes harvested. One eye of each animal had its retina isolated, flat-mounted and trypsin digested to reveal the vasculature architecture. Pericyte numbers will be quantified directly using intrinsic DsRed fluorescence as a marker of cell survival. Acellular capillary formation will be quantified using a nuclear counterstain to identify intrinsically fluorescent (GFP) blood vessels with absent nuclei. The second eye harvested from each animal was embedded and cyrosectioned to permit assessment of retinal thickness and morphology by microscopy.

Results

Figure 6C:
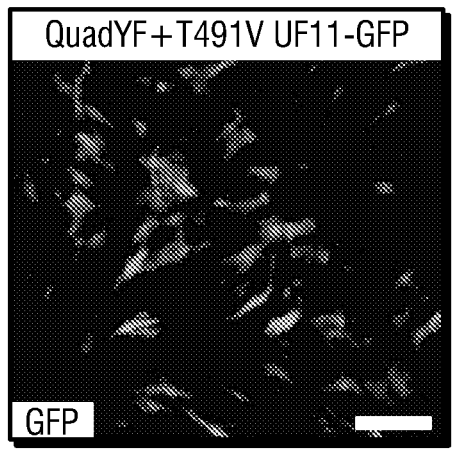
Figure 6C:
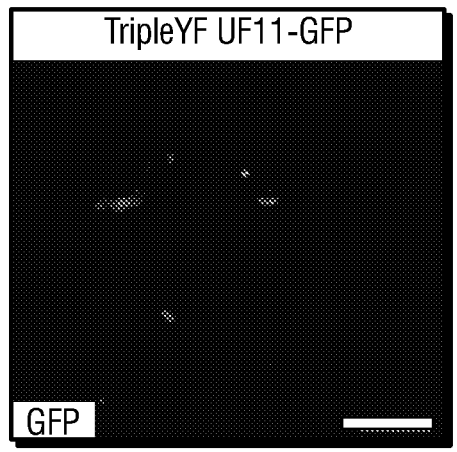
Figure 6C:
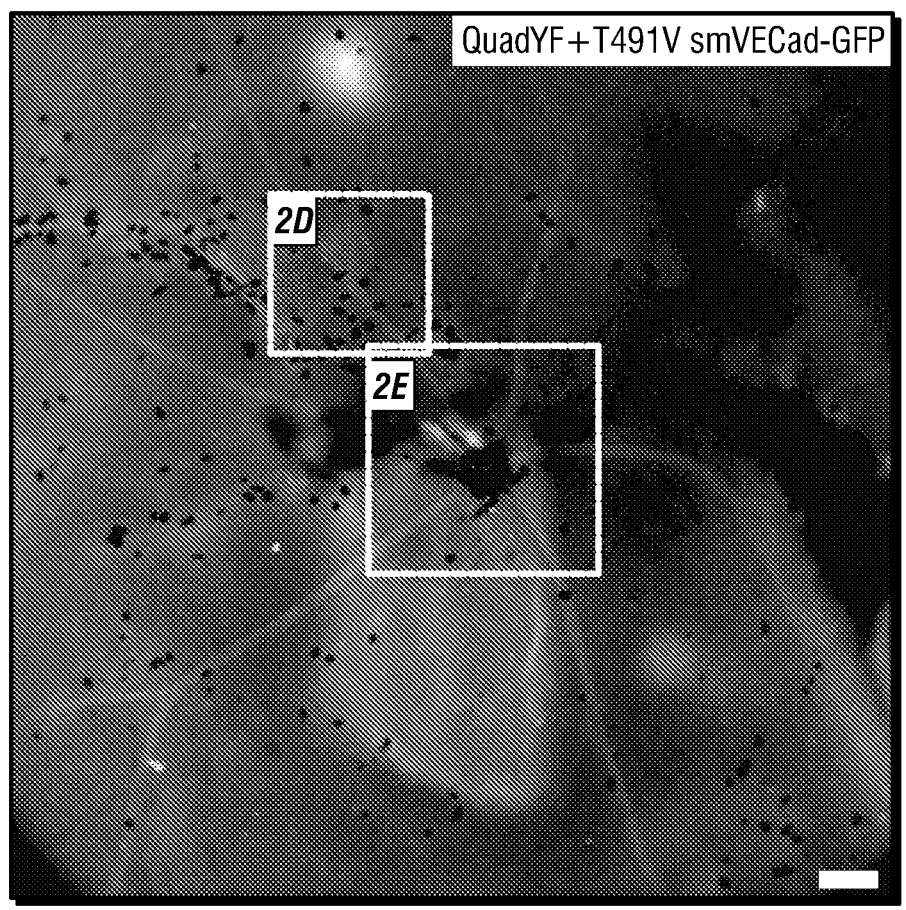
Figure 6D:
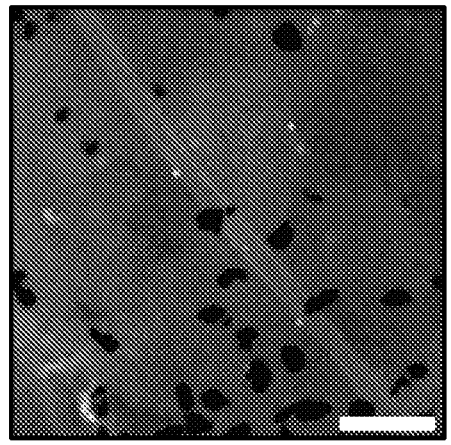
Figure 6E:
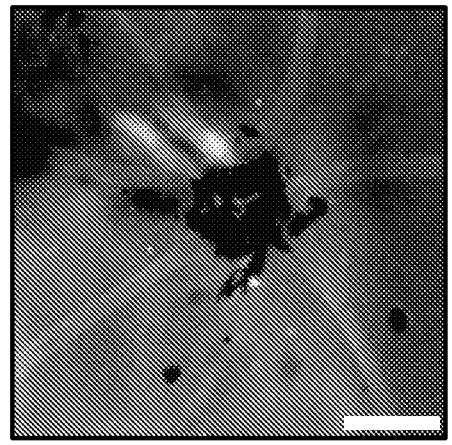

An expression cassette was constructed to express GFP specifically in VECs using a shortened vascular endothelial cadherin (smVECad) promoter. The expression cassette was packaged either into an unmodified AAV2 serotype capsid (AAV2.smVECad-GFP) or into AAV2-derived capsids containing mutated residues that confer altered cellular targeting. Several capsid mutant vectors were assessed in vitro by transduction of primary bovine retinal endothelial cells followed by flow cytometry to quantify cellular GFP expression. The pentuple capsid mutant ("5M") vector (5M.smVECad-GFP) was found to have significantly improved endothelial cell transduction (>70% GFP positive cells) compared to the standard AAV2 serotype (<5%) at equivalent titre (FIG. 6A and FIG. 6B). In vivo transduction of murine retinal vascular endothelial cells was assessed through intravenous (i.v.) administration of the 5m.smVECad-GFP vector in adult wild-type mice followed by post-mortem histology. The vector was purified to high titre ($2.66 \times 10^{13}$ genome particles/mL) and was administered intravenously at several doses (2-, 4-, 8-, 16- or 32-µL) by advancing a 27-gauge needle through the medial canthus into the retro-orbital venous sinus. Four weeks post-injection eyes were harvested and evaluated by fluorescence microscopy for evidence of GFP expression in retinal blood vessels. Injection of 32 µL vector resulted in robust GFP expression in the retinal blood vessels (FIG. 6C, FIG. 6D, and FIG. 6E), indicating that genetic material can be successfully delivered and expressed in vascular endothelial cells following i. v. delivery.

REFERENCES

The following references, to the extent that they provide exemplary procedural or other details supplementary to those set forth herein, are specifically incorporated herein by reference:

ABRAMSON, D H et al., "A phase I/II study of direct intraarterial (ophthalmic artery) chemotherapy with melphalan for intraocular retinoblastoma initial results," *Ophthalmology*, 115:1398-1404, 1404 e1391 (2008).

ACLAND, G M et al., "Gene therapy restores vision in a canine model of childhood blindness," *Nat. Genet.*, 28:92-95 (2001).

BANDELLO, F et al., "Pathophysiology and treatment of diabetic retinopathy," *Acta Diabetol.*, 50(1):1-20 (2013).

COSTA, P Z and SOARES, R, "Neovascularization in diabetes and its complications. Unraveling the angiogenic paradox," *Life Sci.*, 92(22):1037-1045 (2013).

DING, J and WONG, T Y, "Current epidemiology of diabetic retinopathy and diabetic macular edema," *Curr. Diab. Rep.*, 12:346-354 (2012).

EMERGING RISK FACTORS COLLABORATION et al., "Diabetes mellitus, fasting blood glucose concentration, and risk of vascular disease: a collaborative meta-analysis of 102 prospective studies," *Lancet*, 375:2215-2222 (2010).

FISHER, K J et al., "Recombinant adeno-associated virus for muscle directed gene therapy," *Nat. Med.*, 3:306-312 (1997).

FONG, D S et al., "Retinopathy in diabetes," *Diabetes Care*, 27(Suppl 1):S84-S87 (2004).

FORSTERMANN, U and MUNZEL, T, "Endothelial nitric oxide synthase in vascular disease: from marvel to menace," *Circulation*, 113:1708-1714 (2006).

GABRIEL, N et al., "Bioengineering of AAV2 capsid at specific serine, threonine, or lysine residues improves its transduction efficiency in vitro and in vivo," *Hum. Gene Ther. Meth.*, 24:80-93 (2013).

HALBERT, C L et al., "Prevalence of neutralizing antibodies against adeno-associated virus (AAV) types 2, 5, and 6 in cystic fibrosis and normal populations: Implications for gene therapy using AAV vectors," *Hum. Gene Ther.*, 17:440-447 (2006).

HALBERT, C L et al., "Transduction by adeno-associated virus vectors in the rabbit airway: efficiency, persistence, and readministration," *J. Virol.*, 71:5932-5941 (1997).

HAYREH, S S et al., "Central retinal artery occlusion. retinal survival time," *Exp. Eye Res.*, 78:723-736 (2004).

HEITZER, T et al., "Tetrahydrobiopterin improves endothelium-dependent vasodilation by increasing nitric oxide activity in patients with Type II diabetes mellitus," *Diabetologia*, 43:1435-1438 (2000).

HIGASHI, Y et al., "Tetrahydrobiopterin enhances forearm vascular response to acetylcholine in both normotensive and hypertensive individuals," *Am. J. Hypertens.*, 15:326-332 (2002).

HURLBUT, G D et al., "Preexisting immunity and low expression in primates highlight translational challenges for liver-directed AAV8-mediated gene therapy," *Mol. Ther.*, 18:1983-1994 (2010).

JACOBSON, S G et al., "Safety in nonhuman primates of ocular AAV2-RPE65, a candidate treatment for blindness in Leber congenital amaurosis," *Hum. Gene Ther.*, 17:845-858 (2006).

JACOBSON, S G et al., "Safety of recombinant adeno-associated virus type 2-RPE65 vector delivered by ocular subretinal injection," *Mol. Ther.*, 13:1074-1084 (2006).

KAPLITT, M G et al., "Safety and tolerability of gene therapy with an adeno-associated virus (AAV) borne GAD gene for Parkinson's disease: an open label, phase I trial," *Lancet*, 369(9579):2097-2105 (2007).

KAY, C N et al., "Targeting photoreceptors via intravitreal delivery using novel, capsid-mutated AAV vectors," *PLoS One*, 8:e62097 (2013).

LI, Q et al., "Diabetic eNOS-knockout mice develop accelerated retinopathy," *Invest. Ophthalmol. Vis. Sci.,* 51(10):5240-5246 (2010).

MACLAREN, R E et al., "Retinal gene therapy in patients with choroideremia: initial findings from a phase ½ clinical trial," *Lancet,* 383(9923):1129-1137 (2014).

MANNING, W C et al., "Transient immunosuppression allows transgene expression following readministration of adeno-associated viral vectors," *Hum. Gene Ther.,* 9(4):477-485 (1998).

MANNO, C S et al., "AAV-mediated factor IX gene transfer to skeletal muscle in patients with severe hemophilia B," *Blood,* 101(8):2963-2972 (2003).

MANNO, C S et al., "Successful transduction of liver in hemophilia by AAV-Factor IX and limitations imposed by the host immune response," *Nat. Med.,* 12(3):342-347 (2006).

MCPHEE, S W et al., "Immune responses to AAV in a phase I study for Canavan disease," *J. Gene Med.,* 8(5):577-588 (2006).

MEININGER, C J et al. "GTP cyclohydrolase I gene transfer reverses tetrahydrobiopterin deficiency and increases nitric oxide synthesis in endothelial cells and isolated vessels from diabetic rats," *FASEB J.,* 18(15):1900-1902 (2004).

MORI, S et al., "Biodistribution of a low dose of intravenously administered AAV-2, 10, and 11 vectors to cynomolgus monkeys," *Jap. J. Infect. Dis.,* 59:285-293 (2006).

MOSKALENKO, M et al., "Epitope mapping of human anti-adeno-associated virus type 2 neutralizing antibodies: implications for gene therapy and virus structure," *J. Virol.,* 74:1761-1766 (2000).

MOSS, R B et al., "Repeated adeno-associated virus serotype 2 aerosol-mediated cystic fibrosis transmembrane regulator gene transfer to the lungs of patients with cystic fibrosis: a multicenter, double-blind, placebo-controlled trial," *Chest,* 125:509-521 (2004).

MOSS, R B et al., "Repeated aerosolized AAV-CFTR for treatment of cystic fibrosis: a randomized placebo-controlled phase 2B trial," *Hum. Gene Ther.,* 18:726-732 (2007).

NARFSTROM, K et al., "In vivo gene therapy in young and adult RPE65$^{-/-}$ dogs produces long-term visual improvement," *J. Heredity,* 94:31-37 (2003).

PETERSON, E C et al., "Selective ophthalmic artery infusion of chemotherapy for advanced intraocular retinoblastoma: initial experience with 17 tumors," *J. Neurosurg.,* 114:1603-1608 (2011).

PETRS-SILVA, H et al., "High-efficiency transduction of the mouse retina by tyrosine-mutant AAV serotype vectors," *Mol. Ther.,* 17:463-471 (2009).

PETRS-SILVA, H et al., "Novel properties of tyrosine-mutant AAV2 vectors in the mouse retina," *Mol. Ther.,* 19:293-301 (2011).

PIEPER, G M, "Acute amelioration of diabetic endothelial dysfunction with a derivative of the nitric oxide synthase cofactor, tetrahydrobiopterin," *J. Cardiovasc. Pharmacol.,* 29:8-15 (1997).

POIRIER, A E et al., "Toxicology and biodistribution studies of a recombinant adeno-associated virus 2 (rAAV2) alpha-1 antitrypsin (AAT) vector," *Mol. Ther.,* 9:S40-S40 (2004).

SHINOZAKI, K et al., "Oral administration of tetrahydrobiopterin prevents endothelial dysfunction and vascular oxidative stress in the aortas of insulin-resistant rats," *Circ. Res.,* 87:566-573 (2000).

SONG, S et al., "Intramuscular administration of recombinant adeno-associated virus 2 alpha-1 antitrypsin (rAAV-SERPINA1) vectors in a nonhuman primate model: safety and immunologic aspects," *Mol. Ther.,* 6:329-335 (2002).

STROES, E et al., "Tetrahydrobiopterin restores endothelial function in hypercholesterolemia," *J. Clin. Invest.,* 99:41-46 (1997).

TSENG, Y S and AGBANDJE-MCKENNA, M, "Mapping the AAV capsid host antibody response toward the development of second generation gene delivery vectors," *Frontiers Immunol.,* 5:9 (2014).

VERMA, A et al., "ACE2 and Ang-(1-7) confer protection against development of diabetic retinopathy," *Mol. Ther.,* 20:28-36 (2012).

WAGNER, J A et al., "Safety and biological efficacy of an adeno-associated virus vector-cystic fibrosis transmembrane regulator (AAV-CFTR) in the cystic fibrosis maxillary sinus," *Laryngoscope,* 109:266-274 (1999).

XIAO, W et al., "Gene therapy vectors based on adeno-associated virus type 1," *J. Virol.,* 73:3994-4003 (1999).

ZHONG, L et al., "Next generation of adeno-associated virus 2 vectors: point mutations in tyrosines lead to high-efficiency transduction at lower doses," *Proc. Nat'l. Acad. Sci. USA,* 105(22):7827-7832 (2008).

ZHONG, L et al., "Tyrosine-phosphorylation of AAV2 vectors and its consequences on viral intracellular trafficking and transgene expression," *Virology,* 381 (2): 194-202 (2008).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including," or "containing," with reference to an element or elements is intended to provide support for a similar aspect or embodiment of the invention that "consists of," "consists essentially of," or "substantially comprises," that particular element or elements, unless otherwise stated or clearly contradicted by context (e.g., a composition described herein as comprising a particular element should be understood as also describing a composition that contains and/or that includes that particular element, unless otherwise explicated stated, or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the invention as defined by the appended claims.

The invention claimed is:

1. A recombinant adeno-associated virion (rAAV) comprising:
   a) a modified capsid protein, wherein the modified capsid protein comprises Y272F, Y444F, Y500F, Y730F, and T491V amino acid substitutions in a wild-type AAV2 capsid protein, and further wherein the transduction efficiency of the virion comprising the modified capsid protein is higher than that of a virion comprising an unmodified wild-type AAV2 capsid protein; and
   b) an expression cassette packaged within the virion, that comprises an isolated polynucleotide comprising a nucleic acid segment that encodes a diagnostic or a therapeutic molecule, wherein the nucleic acid segment is operably linked to a promoter or a control region that expresses the nucleic acid segment in one or more vascular endothelial cells of a mammal, and wherein the promoter comprises a hybrid cytomegalovirus (CMV)/truncated vascular endothelial cadherin (sm-VECad) promoter (CMV/smVECad).

2. The rAAV of claim 1, wherein the nucleic acid segment encodes one or more diagnostic or therapeutic molecules selected from the group consisting of peptides, polypeptides, ribozymes, peptide nucleic acids, siRNAs, RNAis, antisense oligonucleotides, antisense polynucleotides, antibodies, antigen-binding-fragments thereof, and combinations thereof.

3. The rAAV of claim 1, wherein the nucleic acid segment encodes a biologically-active, mammalian GTP cyclohydrolase polypeptide.

4. The rAAV of claim 1, wherein the transduction efficiency of the rAAV in a mammalian vascular endothelial cell, ocular cell, or retinal cell is about 5- to about 20-fold higher than that of a virion expressing an unmodified, wild-type capsid protein.

5. The rAAV of claim 4, wherein the transduction efficiency of the rAAV in a mammalian vascular endothelial cell of the choriocapillaris is about 5- to about 20-fold higher than that of a virion expressing an unmodified, wild-type capsid protein.

6. A composition comprising the rAAV of claim 1; and a pharmaceutically-acceptable buffer, diluent, or excipient.

7. A kit comprising:
   (1) the rAAV of claim 1,
   (2) instructions for using the rAAV in the diagnosis, prevention, treatment or amelioration of one or more symptoms of a defect, deficiency, dystrophy, disease, disorder, injury, trauma or abnormal condition in a mammal, and
   (3) one or more reagents, restriction enzymes, peptides, therapeutics, pharmaceutical compounds, or means for delivery of the rAAV to host cells or to an animal.

8. The kit of claim 7, wherein the defect, deficiency, dystrophy, disease, disorder, injury, trauma, or abnormal condition in a mammal is selected from macular edema, Type I diabetes, vasculitis, hypertension, vascular occlusion, hypercholesterolemia, ischemia, retinopathy, nephropathy, a retinal disorder, an ocular disease, a retinal dystrophy, and any combination thereof.

9. The kit of claim 8, wherein the disease, disorder or abnormal condition is macular edema.

10. A method for expressing a nucleic acid segment that encodes a therapeutic agent in one or more vascular endothelial cells of a mammal, the method comprising: administering to the mammal an rAAV in accordance with claim 1, in an amount and for a time effective to express the encoded therapeutic agent in the one or more vascular endothelial cells of the mammal.

11. The method of claim 10, wherein the mammal is a human that has, or has been diagnosed with Type I diabetes, vasculitis, endothelial cell dysfunction, microvascular defect, macrovascular defect, diabetic retinopathy, hypertension, vascular occlusion, macular edema, hypercholesterolemia, ischemia, retinopathy, nephropathy, a retinal disorder, disease, or dystrophy, or any combination thereof.

12. The method of claim 10, wherein the therapeutic agent comprises a biologically-active, GTP cyclohydrolase polypeptide.

13. The method of claim 10, wherein the administration is localized or restricted to at least a first portion of the mammalian vasculature, to a selected organ or to a selected tissue thereof, or by direct injection or direct cannulation to the first portion of the mammalian vasculature, including, for example, by direct cannulation or by occlusion of one or more vessels, including to a first portion of the human eye.

* * * * *